United States Patent
Klun et al.

(10) Patent No.: US 10,450,332 B2
(45) Date of Patent: Oct. 22, 2019

(54) STERICALLY HINDERED AMINE AND OXYALKYL AMINE LIGHT STABILIZERS

(71) Applicant: 3M INNOVATIVE PROPERTIES COMPANY, St. Paul, MN (US)

(72) Inventors: Thomas P. Klun, Lakeland, MN (US); Mark A. Roehrig, Stillwater, MN (US); Joseph C. Spagnola, Woodbury, MN (US); Alan K. Nachtigal, Maplewood, MN (US); Charles J. Hoy, Maple Plain, MN (US); Richard J. Pokorny, Maplewood, MN (US); William J. Hunt, Afton, MN (US); Jason T. Petrin, Woodbury, MN (US); Paul B. Armstrong, St. Paul, MN (US); Suresh S. Iyer, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/114,401

(22) Filed: Aug. 28, 2018

(65) Prior Publication Data

US 2018/0362553 A1 Dec. 20, 2018

Related U.S. Application Data

(63) Continuation of application No. 15/528,615, filed as application No. PCT/US2015/065462 on Dec. 14, 2015, now abandoned.

(60) Provisional application No. 62/095,437, filed on Dec. 22, 2014.

(51) Int. Cl.

| | |
|---|---|
| C07F 7/00 | (2006.01) |
| C07F 7/18 | (2006.01) |
| C08K 5/3435 | (2006.01) |
| C09D 7/62 | (2018.01) |
| C08F 222/22 | (2006.01) |
| C09C 3/12 | (2006.01) |
| C08K 3/36 | (2006.01) |
| C08K 9/06 | (2006.01) |

(52) U.S. Cl.
CPC .......... *C07F 7/1804* (2013.01); *C08F 222/22* (2013.01); *C08K 5/3435* (2013.01); *C09C 3/12* (2013.01); *C09D 7/62* (2018.01); *C08K 3/36* (2013.01); *C08K 9/06* (2013.01)

(58) Field of Classification Search
CPC .................................................. C07F 7/1804
See application file for complete search history.

(56) References Cited

U.S. PATENT DOCUMENTS

| | | | |
|---|---|---|---|
| 4,356,296 A | 10/1982 | Griffith | |
| 4,642,126 A | 2/1987 | Zador | |
| 4,648,843 A | 3/1987 | Mitra | |
| 4,652,274 A | 3/1987 | Boettcher | |
| 4,665,217 A | 5/1987 | Reiners | |
| 4,752,338 A | 6/1988 | Reiners | |
| 4,983,737 A | 1/1991 | Ravichandran | |
| 5,026,902 A | 6/1991 | Fock | |
| 5,076,844 A | 12/1991 | Fock | |
| 5,286,865 A | 2/1994 | Galbo | |
| 5,354,808 A | 10/1994 | Onwumere | |
| 5,359,069 A | 10/1994 | Galbo | |
| 5,442,071 A | 8/1995 | Galbo | |
| 6,566,413 B1 | 5/2003 | Weinmann | |
| 6,572,969 B1 | 6/2003 | Samaranayake | |
| 6,624,236 B1 | 9/2003 | Bissinger | |
| 6,852,795 B2 | 2/2005 | Bissinger | |
| 6,852,822 B1 | 2/2005 | Bissinger | |
| 7,101,616 B2 | 9/2006 | Arney | |
| 7,718,264 B2 | 5/2010 | Klun | |
| 9,080,259 B2 | 7/2015 | Schwiegk | |
| 2002/0058735 A1 | 5/2002 | Galbo | |
| 2002/0115754 A1 | 8/2002 | Desai | |
| 2003/0187091 A1 | 10/2003 | Moszner | |
| 2010/0249401 A1 | 9/2010 | Schöning | |
| 2014/0295724 A1 | 10/2014 | Sworen | |
| 2017/0283444 A1 | 10/2017 | Klun | |

FOREIGN PATENT DOCUMENTS

| | | |
|---|---|---|
| EP | 0665233 | 8/1995 |
| EP | 2716666 | 4/2014 |
| GB | 2351732 | 1/2001 |
| JP | 2001-270859 | 10/2001 |
| JP | 2002-284787 | 10/2002 |
| JP | 2007-291340 | 11/2007 |

(Continued)

OTHER PUBLICATIONS

Caragheorgheopol "Using EPR Spectroscopy as a Unique Probe of Molecular-Scale Reorganization and Solvation in Self-Assembled Gel-Phase Materials." Langmuir 2014, 30(30), 9210-9218.*

Amamoto, "Programmed Thermodynamic Formation and Structure Analysis of Star-like Nanogels with Core Cross-linked by Thermally Exchangeable Dynamic Covalent Bonds", Journal of The American Chemical Society, 2007, vol. 129, No. 43, pp. 13298-13304, (XP002754413).

Borch, "The Cyanohydridoborate Anion as a Selective Reducing Agent", Journal of The American Chemical Society, Jun. 16, 1971, vol. 93, No. 12, pp. 2897-2904.

Borch, "Reductive Amination With Sodium Cyanoborohydride: N,N- Dimethylcyclohexylamine", Organic Syntheses, Coll., 1988, vol. 6: p. 499; 1972, vol. 52, p. 124 (5 pages).

(Continued)

*Primary Examiner* — David K O'Dell
(74) *Attorney, Agent, or Firm* — Jean A. Lown

(57) ABSTRACT

Compounds having hindered amine and oxyalkyl amine light stabilizers can mitigate the adverse effects of actinic radiation, such as visible and ultraviolet light, in particular on substrates such as glass or ceramic substrates. Polymers derived from such compounds. Nanoparticles, substrates, such as glass or ceramic substrates, or both nanoparticles and substrates, having such compounds affixed thereto. Articles containing at least one of such polymers, nanoparticles, substrates, or compounds.

11 Claims, No Drawings

(56) References Cited

FOREIGN PATENT DOCUMENTS

| JP | 2010-215902 | 9/2010 |
|---|---|---|
| WO | 2015/051217 | 4/2015 |
| WO | 2016/105974 | 6/2016 |
| WO | 2016/105990 | 6/2016 |
| WO | 2016/105993 | 6/2016 |

OTHER PUBLICATIONS

Jang, "Synthesis and Performance of Reactive Light Stabilizers for Weather-Resistant UV-Curable Coatings", Journal of Industrial and Engineering Chemistry, 2005, vol. 11, No. 6, pp. 964-970, (XP009188746).

Kuroboshi, "Electrooxidation of Alcohols in N-Oxyl-Immobilized Silica Gel/Water Disperse System: Approach to Totally Closed System", Synthesis, Mar. 2009, vol. 2009, No. 6, pp. 903-908, (XP002754414).

Ling, "Synthesis and Characterization of new Monomers and Polymers Containing Hindered Piperidine Groups", Journal of Macromolecular Science, Part A: Pure and Applied Chemistry, 1998, vol. 35, Nos. 7 & 8, pp. 1327-1336.

Ling, "Synthesis And Polymerization Of New Methacryloyl Ureas Carrying A Hindered Piperidine and A Hydroxyl Group", Journal of Macromolecular Science, Part A: Pure and Applied Chemistry, 2001, vol. 38, No. 2, pp. 137-158.

Negishi, "Superior Light Stabilization Using A Novel Hindered Amine Light Stabilizer", Addcon World 2007, International Plastics Additives and Compounding Conference, 13th, Frankfurt, Germany, Sep. 5-6, 2007, Smithers Rapra Technology, Ltd., Shrewsbury, UK, pp. 9/1-9/8, (XP008176823).

Omura, "Oxidation of Alcohols By "Activated" Dimethyl Sulfoxide. A Preparative, Steric And Mechanistic Study", Tetrahedron, 1978, vol. 34, No. 11, pp. 1651-1660.

Schoening, "Synthetic Studies on N-Alkoxyamines: A Mild and Broadly Applicable Route Starting from Nitroxide Radicals and Aldehydes", Journal of Organic Chemistry, Feb. 2009, vol. 74, No. 4, pp. 1567-1573, (XP002754415).

Tidwell, "Oxidation of Alcohols by Activated Dimethyl Sulfoxide and Related Reactions: An Update", Synthesis, Oct. 1990, vol. 1990, No. 10, pp. 857-870.

International Search Report for International Application No. PCT/US2015/065462, dated Mar. 4, 2016, 5 pages.

An, "Improvement in Weatherability of Transparent Plastics by Sol-Gel Coating with UV Absorber and HALS", Journal of Polymer Engineering, Mar. 2009, vol. 29, Nos. 1-3, pp. 51-62.

* cited by examiner

STERICALLY HINDERED AMINE AND OXYALKYL AMINE LIGHT STABILIZERS

CROSS REFERENCE TO RELATED APPLICATIONS

This application is a continuation application of pending prior application Ser. No. 15/528,615, filed May 22, 2017, which is a national stage filing under 35 U.S.C. 371 of PCT/US2015/065462, filed Dec. 14, 2015, which claims the benefit of U.S. Provisional Application No. 62/095,437, filed Dec. 22, 2014, the disclosures of which are incorporated by reference in their entireties herein.

TECHNICAL FIELD

The present disclosure relates to sterically hindered alkyl amine and sterically hindered oxyalkyl amine compounds.

BACKGROUND

Compounds containing sterically hindered alkyl amines or sterically hindered oxyalkyl amines, and particularly the moiety

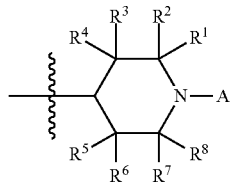

wherein $R^1$ is alkyl, $R^2$ is alkyl, $R^3$ is H or alkyl, $R^4$ is H or alkyl, $R^5$ is H or alkyl, $R^6$ is H or alkyl, $R^7$ is alkyl, and $R^8$ is alkyl are known in the art. When A is alkyl, such compounds are known as hindered amine light stabilizers, or HALS; when A is oxyalkyl, such compounds are known as NORHALS.

The utility of HALS and NORHALS as radical scavengers and polymer stabilizers and is well recognized in the art, and is described in, for example, the Journal of Macromolecular Science Part A, 35:7, 1327-36 (1998) and The Journal of Macromolecular Science Part A, 38:2, 137-58 (2001), as well as in JP 2001270859, U.S. Pat. No. 4,983,737 (Grant), and U.S. Pat. No. 5,442,071 (Grant). Such compounds are known to mitigate the adverse effects of actinic radiation, such as visible and ultraviolet light.

SUMMARY

A compound having the structure of Formula (I) is provided

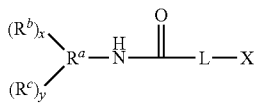

(I)

wherein:
X is

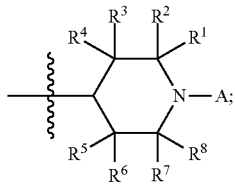

$R^1$ is alkyl;
$R^2$ is alkyl;
$R^3$ is H or alkyl;
$R^4$ is H or alkyl;
$R^5$ is H or alkyl;
$R^6$ is H or alkyl;
$R^7$ is alkyl;
$R^8$ is alkyl;
A is alkyl or oxyalkyl;
L is O or NR';
R' is H or $C_1$ to $C_4$ alkyl;
x is 0-5 and y is 1-6, with the proviso that x+y is no greater than 6;
$R^a$ is a connecting group having a valence of x+y+1;
$R^b$ is an (alkyl)acrylolyoxy functional group of the formula $OC(O)C(R^d)=CH_2$, wherein each $R^d$ is independently selected from alkyl and H;
$R^c$ is selected from $R^9$ and $-OC(O)CH(R^d)CH_2N(R^{10}R^9)_p(R^{11})_q$;
$R^9$ is $-Si(R^{12})_3$;
$R^{12}$ is selected from oxyalkyl, hydroxyl, $OC(O)R^d$, and alkyl with the proviso that at least one $R^{12}$ is oxyalkyl, $OC(O)R^d$, or hydroxyl;
$R^{10}$ is alkylene bound to $R^9$ and the N atom of the $-OC(O)CH(R^d)CH_2N$ moiety;
$R^{11}$ is alkyl or H bound to the N atom of the $-OC(O)CH(R^d)CH_2N$ moiety;
p represents the number of $R^{10}R^9$ groups, which can be 1 or 2; and
q represents the number of $R^{11}$ groups, which can be 0 or 1, with the proviso that the sum of p and q is 2.

DETAILED DESCRIPTION

Throughout this disclosure, singular forms such as "a," "an," and "the" are often used for convenience; however, it should be understood that the singular forms are meant to include the plural unless the singular alone is explicitly specified or is clearly indicated by the context.

Some terms used in this application have special meanings, as defined herein. All other terms will be known to the skilled artisan, and are to be afforded the meaning that a person of skill in the art at the time of the invention would have given them.

"Independently," when used in reference to the identity of one or more variable elements, means that each occurrence of any of the variable elements may have the same or different identity, within the specified limitations, regardless of the identity of any other occurrence of the reference element. Thus, if there are two occurrences of element "X," and element X can be independently selected from identity Y or identity Z, each of the two occurrences of X can be either Y or Z, in any combination (e.g., YY, YZ, ZY, or ZZ).

"Alkyl" refers to an aliphatic hydrocarbon radical. Many alkyl groups are from $C_1$ to $C_{30}$. Some alkyl groups can be $C_1$ or greater, such as $C_2$ or greater, $C_4$ or greater, $C_6$ or greater, or $C_8$ or greater. Some alkyl groups can be $C_{22}$ or smaller, $C_{16}$ or smaller, $C_{12}$ or smaller, $C_8$ or smaller, or $C_4$ or smaller. Unless otherwise indicated, any alkyl group can independently be linear, branched, cyclic, or a combination thereof (e.g., a cyclic alkyl can also have a linear or branched component.) Exemplary alkyl groups include methyl, ethyl, propyl, isopropyl, n-butyl, t-butyl, sec-butyl, iso-butyl, 2-ethyl hexyl, iso-octyl, n-octyl, dodecyl, hexadecyl, behenyl, and the like.

"Oxyalkyl" refers to a monovalent radical having the formula O-alkyl, which can be referred to as an alkoxy group. The alkyl portion of the oxyalkyl can be any alkyl, such as those discussed above with reference to the definition of the term alkyl. Oxyalkyl can be written using standard prefixes to indicate the number of carbon atoms in the alkyl portion of the oxyalkyl. For example, oxymethyl is an oxyalkyl wherein the alkyl portion has one carbon, oxyethyl is an oxyalkyl wherein the alkyl portion has two carbons, etc. Oxyoctyl is an exemplary oxyalkyl that is often used in the compounds described herein.

"Alkylene" refers to an aliphatic hydrocarbon diradical (i.e., divalent radical). Many alkylene diradicals are from $C_1$ to $C_{30}$. Alkylene diradicals can be $C_1$ or greater, $C_2$ or greater, $C_3$ or greater, $C_4$ or greater, $C_6$ or greater, or $C_8$ or greater. Alkylene diradicals can be $C_{22}$ or smaller, $C_{16}$ or smaller, $C_{12}$ or smaller, $C_{10}$ or smaller, or $C_8$ or smaller. Unless otherwise indicated, any alkylene can be linear, branched or cyclic or a combination thereof (e.g., having both a cyclic component and a linear component.) Exemplary alkylene groups include methylene, ethylene, propyl, isopropylene, n-butylene, t-butylene, sec-butylene, iso-butylene, 2-ethylhexylene, iso-octylene, dodecylene, hexadecylene, behenylene, and the like.

"Isocyanate" refers to a molecule comprising at least one isocyanato radical, which is a —NCO radical.

A polymer or copolymer is "derived from" a reference compound when the backbone of the polymer or copolymer contains a polymerized form of the reference compound, either by itself or in combination with other polymerized monomers.

A "hydrocarbon polyradical" as used herein is an aliphatic multivalent radical having a valence of at least three and containing only carbon and hydrogen atoms. Hydrocarbon polyradicals can be from $C_1$ to $C_{30}$. Many are $C_1$ or greater, $C_2$ or greater, $C_3$ or greater, $C_4$ or greater, $C_6$ or greater, or $C_8$ or greater. Hydrocarbon polyradicals can be $C_{30}$ or smaller, $C_{22}$ or smaller, $C_{16}$ or smaller, $C_{12}$ or smaller, $C_{10}$ or smaller, or $C_8$ or smaller. In many embodiments, the polyradical is divalent or trivalent.

"Hydroxyl" is the monoradical —OH.

Compounds of Formula (I) can have an L that is O or NR' with R' being H or $C_1$ to $C_4$ alkyl. When L is O, the compound of Formula (I) is a compound of Formula (II). When L is NR', the compound of Formula (I) is a compound of Formula (IIa).

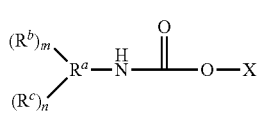

(II)

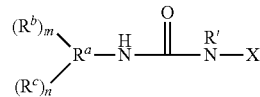

(IIa)

Compounds of Formulas (I) can be synthesized from compounds of Formula (III).

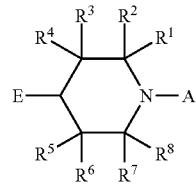

(III)

In the compound of Formula (III), $R^1$ through $R^8$, and A have the same meaning as in the compound of Formula (I), and E is OH or NHR', wherein R' has the same meaning as in the compound of Formula (I).

In any compound of Formula (III), $R^1$, $R^2$, $R^7$, and $R^8$ can be independently any suitable alkyl. $R^1$, $R^2$, $R^7$, and $R^8$ can be the same or different. Typical alkyls for any of $R^1$, $R^2$, $R^7$, and $R^8$ include $C_1$ or greater, $C_2$ or greater, $C_3$ or greater, $C_4$ or greater, $C_6$ or greater, $C_8$ or greater, or $C_{12}$ or greater. Other typical alkyls that can be used as one or more of $R^1$, $R^2$, $R^7$, and $R^8$ include $C_{16}$ or less, $C_{12}$ or less, $C_8$ or less, $C_6$ or less, $C_4$ or less, $C_3$ or less, or $C_2$ or less. In many cases, each of $R^1$, $R^2$, $R^7$, and $R^8$ are methyl.

$R^3$, $R^4$, $R^5$, and $R^6$ can be independently H or alkyl. When one or more of $R^3$, $R^4$, $R^5$, and $R^6$ is alkyl, the alkyl is typically $C_1$ or greater, $C_2$ or greater, $C_3$ or greater, $C_4$ or greater, $C_6$ or greater, $C_8$ or greater, or $C_{12}$ or greater. Such alkyl is often $C_{16}$ or less, $C_{12}$ or less, $C_8$ or less, $C_6$ or less, $C_4$ or less, $C_3$ or less, or $C_2$ or less. In many cases, one or more of $R^3$, $R^4$, $R^5$, and $R^6$ is H. Most commonly, each of $R^3$, $R^4$, $R^5$, and $R^6$ are H.

The identity of each of $R^1$ through $R^8$ in a compound of Formula (III) is carried over into compounds of Formula (I) that are synthesized from that compound of Formula (III). Thus, the identity of each of $R^1$ through $R^8$ in any compound of Formula (I) will depend on, and be the same as, the identity of the $R^1$ through $R^8$ in the compound or compounds of Formula (III) used as a starting material.

In some cases, E in the compound of Formula (III) is hydroxy. When such compound is employed as a starting material, the resulting compound of Formula (I) or Formula (II) will have an L that is O. A can be either alkyl or oxyalkyl. When A is alkyl, then the compound of Formula (III) is a compound of, for example, Formula (IIIa). When A is oxyalkyl, then the compound of Formula (III) is a compound of, for example, Formula (IIIb).

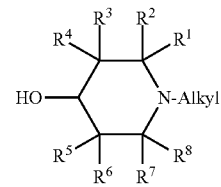

(IIIa)

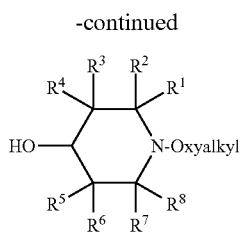

(IIIb)

The alkyl in the compound of Formula (IIIa) can be any suitable alkyl. The alkyl can be linear, branched, cyclic, or a combination thereof (e.g., a cyclic alkyl that also has a linear component). Typical alkyls are $C_1$ or greater, $C_2$ or greater, $C_3$ or greater, $C_4$ or greater, $C_6$ or greater, $C_8$ or greater, or $C_{12}$ or greater. Many alkyls are $C_{16}$ or less, $C_{12}$ or less, $C_8$ or less, $C_6$ or less, $C_4$ or less, $C_3$ or less, or $C_2$ or less. In many cases, the alkyl is $C_1$ to $C_4$ alkyl. Methyl is most common.

Most common compounds of Formula (IIIa) feature $R^1$, $R^2$, $R^7$, and $R^8$ that are methyl, $R^3$, $R^4$, $R^5$, and $R^6$ that are H. In such cases, the compound of Formula (III) is a compound of Formula (IIIa1). The alkyl, which is connected to the nitrogen in the ring, in the compound of Formulas (IIIa) and (IIIa1) is most often methyl. In such cases, the compound of Formula (IIIa1) is a compound of Formula (IIIa2).

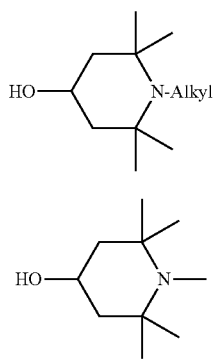

(IIIa1)

(IIIa2)

Most common compounds of Formula (IIIb) feature $R^1$, $R^2$, $R^7$, and $R^8$ that are methyl, and $R^3$, $R^4$, $R^5$, and $R^6$ that are H. In such cases, the compound of Formula (IIIb) is a compound of Formula (IIIb1).

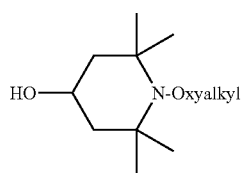

(IIIb1)

The oxyalkyl in the compound of Formula (IIIb) or (IIIb1), which is connected to the nitrogen in the ring, can be any suitable oxyalkyl. The oxyalkyl can be linear, branched, cyclic, or a combination thereof (e.g., a cyclic oxyalkyl can also have a linear component). Typical oxyalkyls are $C_1$ or greater, $C_2$ or greater, $C_3$ or greater, $C_4$ or greater, $C_6$ or greater, $C_8$ or greater, $C_{12}$ or greater, $C_{16}$ or greater, or $C_{22}$ or greater. Many oxyalkyls are $C_{26}$ or less, $C_{22}$ or less, $C_{18}$ or less, $C_{16}$ or less, $C_{12}$ or less, $C_8$ or less, $C_6$ or less, $C_4$ or less, $C_3$ or less, or $C_2$ or less. $C_8$ oxyalkyl is often used. In most cases, compounds of Formula (IIIb) or (IIIb1) contain a mixture of linear and branched isomers of the oxyalkyl group. This effect has been noted in documents that describe the preparation of such compounds, such as Schoening et al. (*J. Org. Chem.*, 2009, 74, 1567-1573), U.S. Pat. Nos. 4,983,737, 5,286,865, 5,442,071 and US 2010/0249401. Of the $C_8$ isomers, which are collectively known as oxyoctyl, branched isomers tend to occur more often than the linear isomer. When the oxyalkyl in the compound of Formula (IIIb1) is oxyoctyl, the compound of Formula (IIIb1) is a compound of Formula (IIIb2).

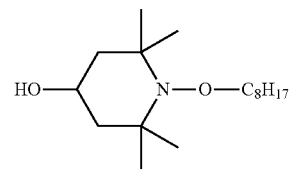

(IIIb2)

In other cases, E in the compound Formula (III) can be NHR'. When such compounds are employed as starting materials, the resulting compounds of Formula (I) or (IIa) will have L that is NR'. In this case, A can be alkyl or oxyalkyl. When A is alkyl, the compound of Formula (III) is a compound of Formula (IV). When A is oxyalkyl, the compound of Formula (III) is a compound of Formula (IVa).

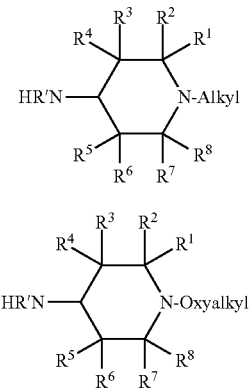

(IV)

(IVa)

In compounds of Formula (IV) and (IVa), the identity of each of R' through $R^8$ is the same as in the compound of Formula (III). Most commonly, compounds of Formula (IV) feature $R^1$, $R^2$, $R^7$, and $R^8$ that are methyl, and $R^3$, $R^4$, $R^5$, and $R^6$ that are H. In such cases, the compound of Formula (IV) is a compound of Formula (IV1).

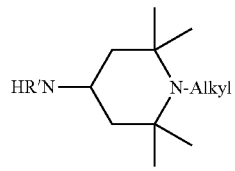

(IV1)

R' in the compound of Formula (IV) or (IV1) can be H or any $C_1$ to $C_4$ alkyl. When R' is alkyl, methyl and ethyl are most common. Typically, R' is H, in which case the compound of Formula (IV1) is a compound of Formula (IV2).

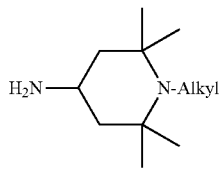
(IV2)

The alkyl, which is connected to the nitrogen in the ring, in the compound of Formula (IV), (IV1), or (IV2) can be any suitable alkyl, such as those discussed above with respect to the compound of Formulas (IIIa). Methyl is most common, in which case the compound of Formula (IV2) is a compound of Formula (IV3).

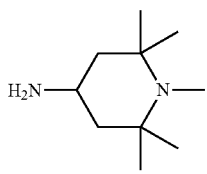
(IV3)

In the compound of Formula (IVa), the identity of each of R' through $R^8$ is the same as in the compound of Formula (III). Most commonly, compounds of Formula (IVa) feature $R^1$, $R^2$, $R^7$, and $R^8$ that are methyl, $R^3$, $R^4$, $R^5$, and $R^6$ that are H. In such cases, the compound of Formula (IVa) is a compound of Formula (IVa1).

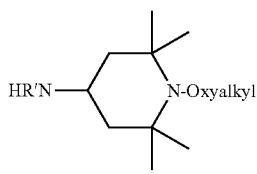
(IVa1)

R' in the compound of Formula (IVa) or (IVa1) can be H or any $C_1$ to $C_4$ alkyl. When R' is alkyl, methyl and ethyl are most common. Typically, R' is H, in which case the compound of Formula (IVa1) is a compound of Formula (IVa2).

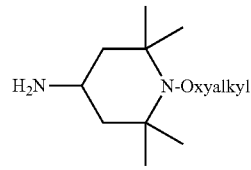
(IVa2)

In the compounds of Formulas (IVa), (IVa1), and (IVa2) the oxyalkyl, which is connected to the nitrogen in the ring, can be any suitable oxyalkyl, such as those discussed above with respect to the compound of Formula (IIIb). Oxyoctyl is most common, in which case the compound of Formula (IVa2) is a compound of Formula (IVa3).

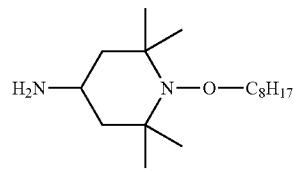
(IVa3)

The various compounds of Formula (III) discussed herein can be used in the synthesis of compounds of Formulas (I) or (II). Those compounds featuring and E that is OH are useful in preparing compounds of Formula (I) or (II), whereas those featuring and E that is NHR' are useful for preparing compounds of Formula (I) or (IIa).

For example, compounds of Formula (IIIa) can be used as starting materials for compounds of Formula (I) or (II) wherein A is alkyl and L is O. Typically, compounds of Formula (IIIa2) are used for this purpose. Exemplary compounds of Formula (IIIa), (IIIa1), and (IIIa2) can be obtained from TCI America (OR, USA), for example, under the trade designation PMHP.

As another example, compounds of Formula (IIIb), (IIIb1), and (IIIb2) can be used as starting materials for compounds of Formula (I) or (II) wherein A is oxyalkyl and L is O. Compounds of Formula (IIIb) are sometimes known as alkylated N-oxyalkyl 4-hydroxy piperidines, and can be prepared from commercially available bis(alkyated N-oxyalkyl-4-piperidyl) esters of alkylene diacids as shown in Reaction Scheme 1. Exemplary bis(alkylated N-oxyalkyl-4-piperidyl) esters of alkylene diacids can be obtained from BASF (NJ, USA), for example, under the trade designation TINUVIN 123.

Reaction Scheme 1

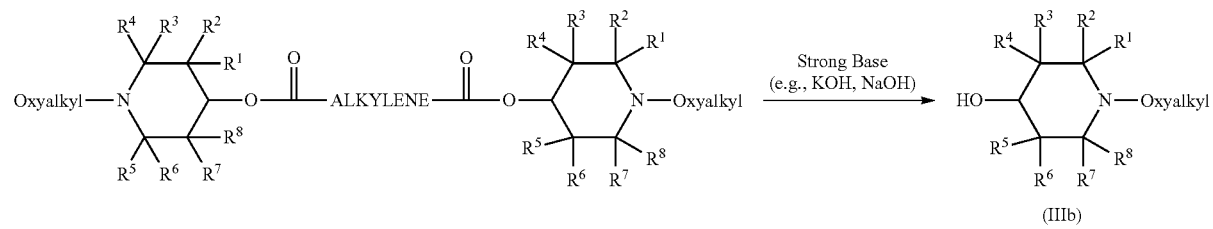
(IIIb)

As shown in Reaction Scheme 1, treating a bis(alkylated N-oxyalkyl-4-piperidyl) ester of alkylene diacids with a strong Arrhenius base, for example an alkali metal hydroxide such as potassium hydroxide or sodium hydroxide, hydrolyzes the esters to form an alkylated N-oxyalkyl 4-hydroxy piperidine. This reaction can take place under any suitable conditions for hydrolyzing diacids. The reaction often takes place in the presence of one or more inert diluents. The one or more inert diluents are typically used to dissolve or disperse the strong Arrhenius base, the bis (alkylated N-oxyalkyl-4-piperidyl) esters of alkylene diacids, or both. Typical inert diluents include alcohols, such as methanol, ethanol, or isopropanol. The reaction can be promoted by heating. When one or more alcohols are used as the inert diluents, heating can involve refluxing the one or more alcohols. The starting material of Reaction Scheme 1 is often a bis(2,2,6,6-tetramethyl-N-oxyalkyl-4-piperidyl) ester, in which case the product of Reaction Scheme 1 is the compound of Formula (IIIb2).

Compounds of Formula (IV), including compounds of Formula (IV1), (IV2), and (IV3), can be used as starting materials for compounds of Formula (I) wherein A is alkyl and L is NR'. Compounds of Formula (IVa), including compounds of Formulas (IVa1), (IVa2), and (IVa3), can be used as starting materials for compounds of Formula (I) wherein A is oxyalkyl and L is NR'.

Compounds of Formula (IV) and (IVa) wherein R' is H can be synthesized from compounds of Formula (IIIa) or (IIIb), respectively, as shown in Reaction Scheme 2 and Reaction Scheme 3. First, compounds of Formulas (III) or (IIIa) can be converted to ketone intermediates of Formula (IIIb) or (IIIc) by Swern oxidation of the hydroxy group in the compounds of Formula (III) with oxalyl chloride and dimethyl sulfoxide (DMSO) followed by quenching with triethylamine. The ketone intermediates of Formula (IIIc) or (IIId) can then be converted to compounds of Formula (V) or (Va), respectively, by reductive amination. Reductive amination can be accomplished by any suitable procedure, such as treatment with sodium cyanoborohydride and ammonia or an amine, which is typically a protonated ammonia (an ammonium salt such as ammonium acetate) or protonated amine.

The nature of the amine used in the reductive amination reaction determines the identity of R' in the compound of Formula (IV) or (IVa) (the NH$_2$ group would be NR'H). Thus, if ammonium is used, as in Reaction Scheme 2, R' in the resulting compound is H.

Reaction Scheme 2

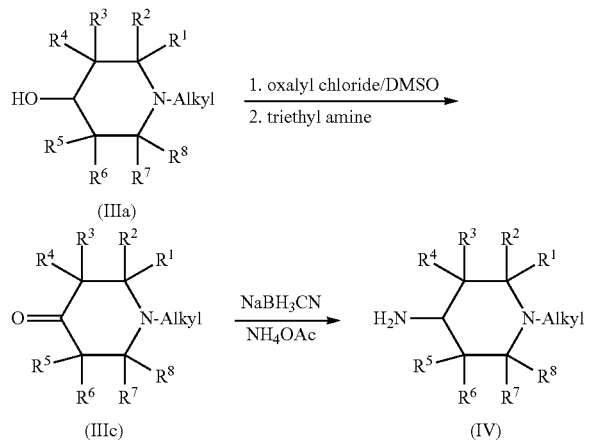

(IIIa)

(IIIc)

(IV)

-continued
Reaction Scheme 3

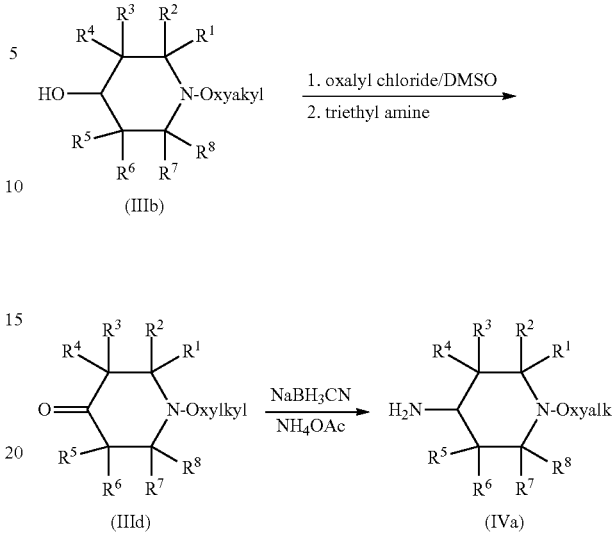

(IIIb)

(IIId)

(IVa)

Conditions for Swern oxidation of alcohols to ketones are known to people of ordinary skill in the art, and have been disclosed, for example, in "Oxidation of alcohols by 'activated' dimethyl sulfoxide. A preparative, steric and mechanistic study", Tetrahedron, 34 (11), 1978 (Omura et al.), and "Oxidation of alcohols by activated dimethyl sulfoxide and related reactions: An update", Synthesis, (10); 857-70 (Tidwell et al.). Conditions for reductive amination of carbonyls with sodium cyannoborohydride are also known to people of ordinary skill in the art, and have been disclosed, for example, in "Reductive amination with sodium cyanoborohydride: N,N-dimethylcyclohexylamine", Org. Synth. Coll., Vol. 6: 499, 1988 (Borch), and "Cyanohydriodoborate anion as a selective reducing agent", J. Am. Chem. Soc., 95 (12), 1971 (Borch et al.).

As discussed above, one method to provide compounds of Formula (V) or (Va) wherein R' is C$_1$ to C$_4$ alkyl is the use of a primary alkyl amine compound in the reductive amination reaction. As an alternative, compounds of Formulas (V) or (Va) can be alkylated by reaction of the primary amine with a compound of Formula (VI), as shown in Reaction Schemes 4 and 5. The resulting compounds wherein R' is C$_1$ to C$_4$ alkyl are compounds of Formula (IVb) or (IVc). The chemical structure of compounds of Formula (IVb) and (IVc) is identical whether such compounds are made by reductive amination with a primary alkyl amine in a process similar to Reaction 2 or 3 as shown above or by alkylation as shown in Reaction Schemes 4 and 5.

Reaction Scheme 4

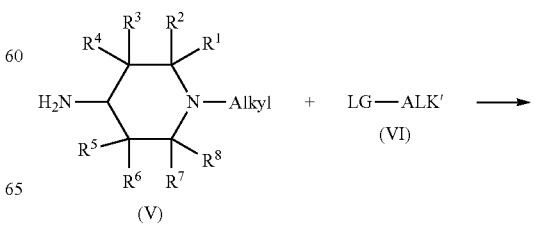

(V)

-continued

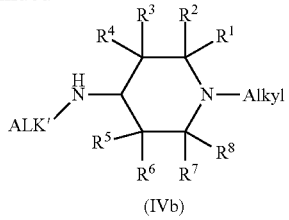

(IVb)

Reaction Scheme 5

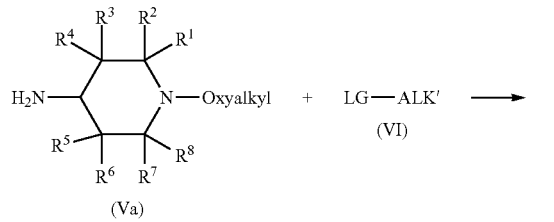

(IVc)

In the compound of Formulas (VI), ALK' is $C_1$ to $C_4$ alkyl and LG is a leaving group. Any suitable leaving group that can be used, so long as the compound of Formula (VI) is reactive with the exocyclic amine of a compound of Formulas (V) or (Va). Suitable leaving groups include halide, such as chloride, bromide, and iodide, mesylate, tosylate, and the like. Likewise, ALK' any suitable $C_1$ to $C_4$ alkyl can be used. Typical examples of $C_1$ to $C_4$ alkyl include methyl, ethyl, n-propyl, iso-propyl, and n-butyl. Methyl and ethyl are most common.

The ALK' moiety in the compounds of Formulas (IVb) and (IVc) comes from the ALK' group of compounds of Formula (VI), and is defined in the same way as that in compounds of Formula (VI).

The reaction shown in Reaction Schemes 4 and 5 can take place under any reaction conditions suitable for alkylation of a primary amine. Typically, the compound of Formula (V) or (Va) is first dissolved or dispersed in one or more inert diluents that do not undergo a chemical reaction under the alkylation conditions. Common inert diluents include aromatics such as benzene, toluene, and xylenes, ethers such as diethyl ether and tetrahydrofuran, as well as hydrocarbons such as hexanes. The compound of Formula (VI) can be added to the compound of Formula (V) or (Va) and the inert diluents in any suitable manner. For example, the compound of Formula (VI) can be added to the compound of Formula (V) or (Va) and the one or more inert diluents dropwise with a syringe. The reaction often takes place at ambient temperatures, but it can be facilitated by heating if necessary.

Compounds of Formulas (I), (II), and (IIa) can be produced by at least two approaches. The first approach, which is particularly useful for making compounds of Formula (I), (II), or (IIa) wherein $R^c$ is $R^{10}(R^9)_p$, involves forming an acrylate intermediate by reacting a compound of Formula (III), including any compound of Formula (IIIa), (IIIa1), (IIIa2), (IIIb), (IIIb1), (IIIb2), or a compound of Formula (IV), including any compound of Formula (IVa), (IV1), (IV2), (IV3), (IVa1), (IVa2), or (IVa3), with an isocyanate compound of Formula (V). Some variations of this reaction are shown in Reaction Schemes 6, 7, 8, 9, and 10, which depict the reaction of compounds of Formulas (III), (IIIa), (IIIb), (IV), and (IVa) respectively, with a compound having the formula $(R^b)_m$—$R^a$—NCO.

In the isocyanate compound of structure $(R^b)_m$—$R^a$—NCO, each $R^b$ is an (alkyl)acryloyloxy group, which means that each group is alkylacryloyloxy group or acrylolyloxy group. The alkylacryloyloxy group (—OC(O)C($R^d$)=$CH_2$) is typically methacrylolyoxy. The variable m refers to the number of (alkyl)acryloyloxy groups and can be any integer but is usually in a range of 1 to 6 or in a range of 1 to 3. In many embodiments, m is equal to 1 or 2. The group $R^a$ is a divalent radical (i.e., one $R^b$ group), a trivalent radical (i.e., two $R^b$ groups), or a higher polyvalent radical (i.e., 3 or more $R^b$ groups). In many embodiments $R^a$ is divalent or trivalent. If $R^a$ is divalent, $R^a$ is often an alkylene (i.e., an alkane-diyl). If $R^a$ is trivalent, $R^a$ is often an alkane-triyl.

Reaction Scheme 6

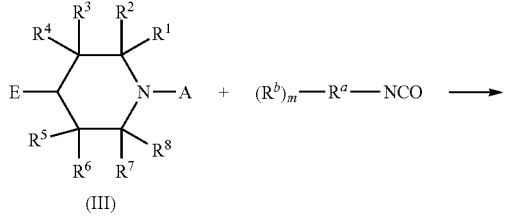

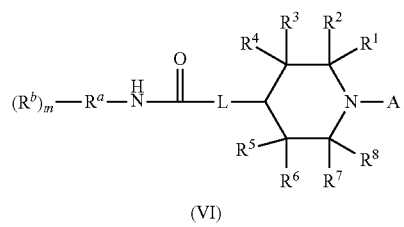

(VI)

Reaction Scheme 7

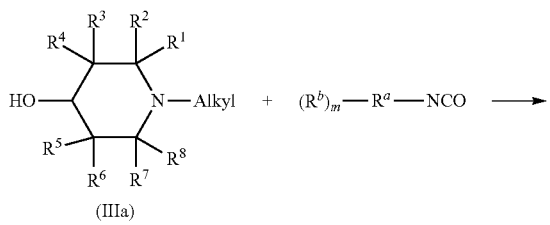

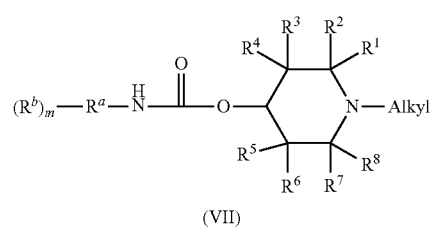

(VII)

Reaction Scheme 8

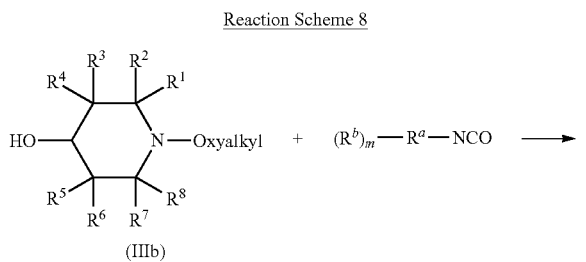

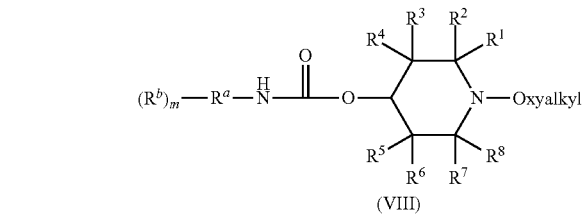

Reaction Scheme 9

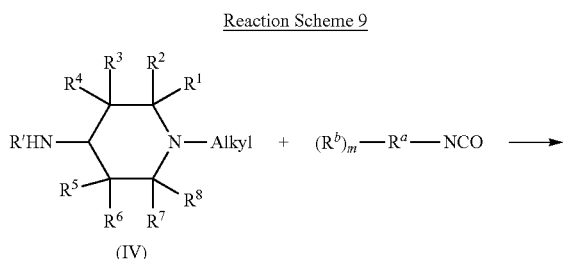

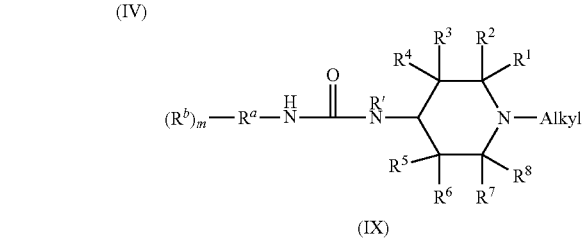

Reaction Scheme 10

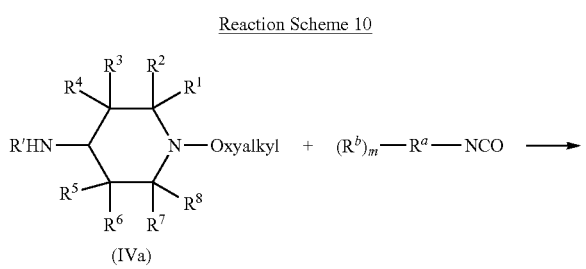

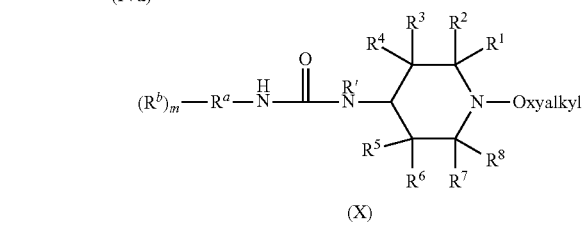

The reactions of Reaction Schemes 6, 7, 8, and 9 can take place under any conditions that are suitable for the condensation of an alcohol with an isocyanato group, such as the isocyanate compounds shown in those Schemes. Typically, the starting materials are dried, admixed, and stirred until the reaction is complete. The progress of the reaction can be monitored by removing aliquots of the reaction mixture and analyzing the aliquots by Fourier transform infrared spectroscopy (FTIR). When FTIR no longer shows a prominent isocyanate absorption (typically at about 2250 $cm^{-1}$ to about 2275 $cm^{-1}$, such as at 2265 $cm^{-1}$), then the reaction is complete. The reaction can be carried out in one or more inert diluents that dissolve or disperse one or more of the starting materials or products, but do not undergo chemical reaction under the reaction conditions. Typical inert diluents include ethers such as diethyl ether and tetrahydrofuran, ketones such as acetone and methyl ethyl ketone, and aromatics such as benzene and toluene. If needed, the reaction mixture can be heated, for example to a temperature between 50° C. and 70° C., to facilitate the reaction. When the reaction is heated, it is often convenient to use an inert diluent that can reflux at the desired temperature in order to maintain that temperature. The reaction is often carried out under a dry atmosphere in order to minimize unwanted side reactions.

A catalyst can be used to accelerate the reactions depicted in Reaction Schemes 6-10, such as a compound of Formula (IIIa), (IIIb), (IV), or (IVa). Suitable catalysts include, but are not limited to, amines and tin compounds. Examples of useful tin compounds include tin (II) and tin (IV) salts, such as stannous octoate, dibutyltin dilaurate, dibutyltin diacetate, dibutyltin di-2-ethylhexanoate, and dibutyltin oxide. Examples of useful amine compounds include tertiary amines such as triethylamine, tributylamine, triethylenediamine, tripropylamine, bis(dimethylaminoethyl)ether, morphonilin compounds such as ethyl morpholine, and 2,2'-dimorpholinodiethyl ether, 1,4-diazobicyclo[2.2.2]oxtane and 1,8-diazobicyclo[5.4.0]undec-7-ene (available from Aldrich Chemical Co., Milwaukee, Wis., USA, under the trade designations DABCO and DBU, respectively). In many cases, both a tin catalyst and an amine catalyst are used.

The catalyst, if employed, can be used in any suitable amount. Typically, the amount of tin catalyst is from about 50 to about 100,000 parts per million based on the total solids in the reaction, with a level of about 100 to 1,000 parts per million being most common. Amine catalysts are typically used at a level of about 0.001 to about 1 mol of amine per mol of the compound of Formula (III).

Catalysts such as those discussed above can be necessary to promote the reaction of a compound of Formula (III) with an isocyanate compound when E is OH. Thus, catalysts, usually tin catalysts such as those discussed above, are often used with the reaction of (IIIa) or (IIIb), that is, in Reaction Schemes 8 and 9. Amine catalysts and tin catalysts are often used together in such cases. In other cases, the catalyst may not be necessary to promote the reaction.

The compound having the formula $(R^b)_m$—$R^a$—NCO is a isocyanate compound that comprises both an (alkyl) acrylolyoxy group and an isocyanato group. The variable m represents the number of (alkyl)acrylolyoxy groups, $R^b$, that are attached to the connecting group $R^a$. In the compound of Formula (V), both $R^a$ and $R^b$ are defined as above. Many compounds of Formula (V) are commercially available, for example, from CBC America Corp. (Commack, USA) or Sigma-Aldrich (Milwaukee, USA). Such compounds include 2-isocyanatoethyl methacrylate, 2-isocyanatoethyl acrylate, 1,1-bis(acryloyloxymethyl)ethyl isocyanate, and the like. Such compounds most often feature a value of m that is 1 or 2. Compounds of Formula (V) featuring a value of m that is 2 are most commonly used.

The product of Reaction Scheme 6 is a compound of Formula (VI). In compounds of Formula (VI), R' through $R^8$ and A are carried over from the compound of Formula (III) that is used in Reaction Scheme 6. Thus, R' through $R^8$ and A have the same identity in compounds of Formula (VI) as in compounds of Formula (III). Likewise, $R^a$, $R^b$, and m are carried over from the isocyanate compound that is used in Reaction Scheme 6. The identity of $R^a$, $R^b$, and m are therefore the same as those in the isocyanate compound that is used in Reaction Scheme 6. The identity of L in the compound of Formula (VI) depends on, but is not the same as, the identity of E in the compound of Formula (III) that is used in Reaction Scheme 6. When a compound of Formula (III) having an E that is OH is used in Reaction Scheme 6, then L in the resulting compound of Formula (VI) is O. When a compound of Formula (III) having an E that is NR'H is used in Reaction Scheme 6, then L in the resulting compound of Formula (VI) is NR'. In such cases, the identity of R' in the compound of Formula (VI) is identical to the identity of R' in the compound of Formula (III) that is used in Reaction Scheme 6.

Reaction Schemes 7 and 8 shows the reaction of a compound of Formulas (IIIa) and (IIIb), respectfully, with an isocyanate compound. The products of these reactions are compounds of Formulas (VII) and (VIII), respectfully. Compounds of Formula (VII) are compounds of Formula (VI) wherein L is O and A is alkyl. Thus, the identity of R' through $R^8$, $R^a$, $R^b$, and m are as described above with respect to Formula (VI). Similarly, compounds of Formula (VIII) are compounds of Formula (VI) wherein L is O and A is oxyalkyl. In such compounds, the identity of $R^1$ through $R^8$, $R^a$, $R^b$, and m are as described above with respect to Formula (VI).

The product of Reaction Schemes 9 and 10 are compounds of Formula (IX) or (X), respectively. Compounds of Formula (IX) are compounds of Formula (VI) wherein L is NR' and A is alkyl. In such compounds, the identity of $R^1$ through $R^8$, $R^a$, $R^b$, R', and m are as described above with respect to Formula (VI). Similarly, compounds of Formula (X) are compounds of Formula (VI) wherein L is NR' and A is alkyl. In such compounds, the identity of $R^1$ through $R^8$, $R^a$, $R^b$, R', and m are as described above with respect to Formula (VI).

Any compound of Formulas (VI), (VII), (VIII), (XI), or (X) can be converted into a compound of Formula (I) by reacting the carbon-carbon double bond of one or more of the $R^b$ groups with an amino silane compound of Formula (XI). Reaction Scheme 11 illustrates this reaction between a compound of Formula (VI) and a compound of Formula (XI) to produce a compound of Formula (XII).

Reaction Scheme 11

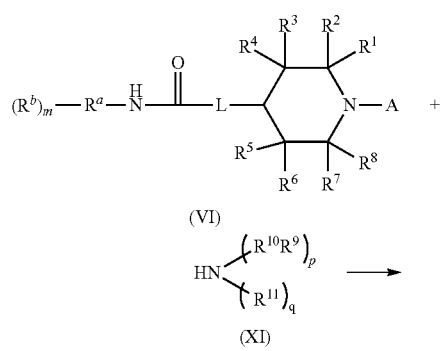

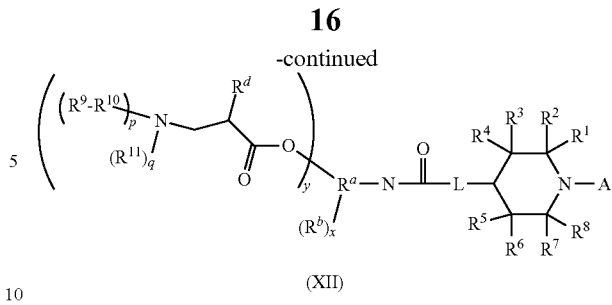

In the compound of Formula (XI), $R^9$, $R^{10}$, and $R^{11}$ are defined as discussed above with respect to Formula (I). $R^9$, which is —Si($R^2$)$_3$, features three $R^{12}$ groups; in many cases, at least one of these $R^{12}$ groups is oxyalkyl. $C_1$ to $C_6$ oxyalkyl is most often employed, with oxymethyl and oxyethyl being most common. Typically, all three $R^{12}$ groups are oxyalkyl, such as the oxyalkyl groups discussed previously. However, in some cases one or more of the $R^{12}$ groups are alkyl, OC(O)$R^d$ or hydroxyl. When one or more of the $R^{12}$ groups are alkyl, the alkyl is typically $C_1$ to $C_6$ alkyl, with methyl and ethyl being most common. When one or more of the $R^{12}$ are OC(O)$R^d$, $R^d$ is typically H or $C_1$ to $C_6$ alkyl, with $C_1$ to $C_6$ alkyl being more common than H and methyl and ethyl being most common.

In the compound of Formula (XI), each $R^{1'}$ can be any alkylene, but is typically $C_1$ to $C_{12}$ alkylene, such as $C_1$ to $C_6$ alkylene. Propylene is commonly used. Likewise, when an $R^{11}$ group is present, it can be either H or any alkyl group. When alkyl is used, it is typically $C_1$ to $C_{12}$ alkyl, such as $C_1$ to $C_6$ alkyl, with methyl being most common.

In the compound of Formula (XI), p is 1 or 2 and q is 0 or 1 such that the sum of p and q is 2. Thus, the amine in this compound can be a primary amine in the case that p is 1, q is 0 and $R^{11}$ is H, or a secondary amine in all other cases. This is because tertiary amines can have low reactivity with the $R^b$ groups in compounds of Formula (VI).

Many compounds of Formula (XI) are known in the art and are commercially available. For example, 3-aminopropyltriethoxysilane (DYNASYLAN AMEO), 3-aminopropylmethyldiethoxysilane (DYNASYLAN 1505), 3-aminopropyltrimethoxysilane (DYNASYLAN AMMO), N-(n-butyl)-3-aminopropyltrimethoxysilane (DYNASYLAN 1189), 2-aminoethyl-3-aminopropyltrimethoxysilane (DYNASYLAN DAMO), bis-(3-triethoxysilylpropyl)amine (DYNASYLAN 1122), and bis-(3-trimethoxysilylpropyl)amine (DYNASYLAN 1124) which are all obtainable from Evonik Co. (Piscataway, N.J., USA) under the above-mentioned trade designations. Also, N-methylaminopropyltrimethoxysilane is available from Gelest (Morrisville, Pa., USA) under the trade designation SIM6500.0.

The reaction of Reaction Scheme 11 can proceed under any conditions suitable for adding an amine to the carbon-carbon double bond of an (alkyl)acrylolyoxy group. Typically, the compound of Formula (VI) is heated to a temperature that facilitates the reaction, such as from 40° C. to 80° C., and the compound of Formula (XI) is then added. Addition of the compound of Formula (XI) can take place in a dropwise manner. The reactants are typically stirred at the elevated temperature for sufficient time for the reaction to complete, which is typically no less than twenty minutes and no more than one day after the addition of the compound of Formula (XI) is complete. The progress of the reaction can be monitored by conventional techniques, such as thin layer chromatography, for the disappearance of the compound of Formula (VI), and can be complete when the compound of Formula (VI) is no longer detectable. The reaction often takes place in the presence of an inert diluent. The inert diluent, when used, is typically one or more liquids that do not undergo a chemical transformation under the reaction conditions. Exemplary inert diluents include chlorinated hydrocarbons such as methylene chloride and chloroform, aromatic compounds such as benzene, toluene, and xylenes, and ethers such as tetrahydrofuran, diethyl ether, and methyl butyl ether. In many cases, the reaction proceeds under a dry atmosphere in order to minimize unwanted side reactions. Conducting chemical reactions under dry atmosphere is a technique well known to the person of ordinary skill in the art.

It is not necessary to isolate the compound of Formula (VI) before the reaction of Reaction Scheme 11 takes place. Instead, the compound of Formula (VI) can be formed in situ, for example, according to Reaction Scheme 6 to 10, and the compound of Formula (XI) added directly to the reaction product of Reaction Scheme 6 to 10 without first isolating the reaction product. The reaction with the compound of Formula (XI) can then proceed as described above.

The product of Reaction Scheme 11 is a compound of Formula (XII). Compounds of Formula (XII) are compounds of Formula (I) in which $R^c$ is —OC(O)CH($R^d$)CH$_2$N($R^{10}R^9$)$_p$($R^{11}$)$_q$. In the compound of Formula (XII), the identity of each of $R^a$, $R^b$ (including $R^d$, which is a component of $R^b$), L, $R^1$ to $R^8$, and A follows from the compound of Formula (VI), and are therefore the same as those discussed above with respect to Formula (VI). In most cases, the (alkyl)acrylolyoxy is an acrylate group in which $R^d$ is H, since the addition of the amine is much more facile when $R^d$ is H than when it is alkyl. Likewise, the identity of each of $R^9$, $R^{10}$, and $R^{11}$, as well as the value of p and q, follows from the compound of Formula (XI), and are therefore the same as those discussed above with respect to Formula (XI).

The values of x and y in compounds of Formula (XII) relates to the value of m in the compound of Formula (VI) that is used in Reaction Scheme 11. There are m $R^b$ groups containing an (alkyl)acrylolyoxy moiety in the compound of Formula (VI), each of which either reacts with a compound of Formula (XI) or remains unreacted. Thus, the sum of x and y equals the value of m in the compound of Formula (VI) that is used in Reaction Scheme 11, wherein x represents the number of unreacted $R^b$ groups and y represents the number of $R^b$ groups that react with the compound of Formula (XI).

More than one different type of compound of Formula (XI) can be used in the reaction illustrated in Reaction Scheme 11. When more than one type of compound of Formula (XI) is used, the resulting product of Formula (XII) can feature one or more $R^9$, $R^{10}$, and $R^{11}$ groups having different identities.

Returning to Reaction Scheme 11, the compound of Formula (VI) used therein often features a value of 2 for m and two $R^b$ groups wherein $R^d$ is H. In such cases, the compound of Formula (VI) is a compound of Formula (XIII).

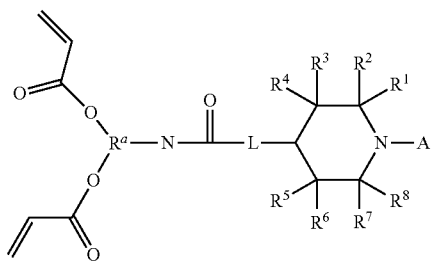

(XIII)

Compounds of Formula (XIII) can be converted into compounds of Formula (I) by reaction with an amino silane compound of Formula (XI) as illustrated in Reaction Scheme 12.

The reaction of Reaction Scheme 12 provides two products: the compound of Formula (XIV) and the compound of Formula (XV). The compound of Formula (XIV) is a mono-adduct of the starting materials, and is a compound of Formula (I), (II), or (IIa) wherein $R^c$ is —OC(O)CH($R^d$)CH$_2$N($R^{10}R^9$)$_p$($R^{10}$)$_q$, x is 1 and y is 1. The formation of this compound can be promoted by using one or fewer equivalents (with respect to the number of acryl groups) of the compound of Formula (XI) in the reaction of Reaction Scheme 12. The compound of Formula (XV) is a di-adduct of the starting materials, and is a compound of Formula (I) wherein $R^c$ is $R^{10}$($R^9$)$_p$, x is 0 and y is 2. The formation of this compound can be promoted by using two or more equivalents of the compound of Formula (XI) in the reaction of Reaction Scheme 12.

In the compounds of Formulas (XIV) and (XV), the identity of the unspecified variables are identical to that discussed above with respect to compounds of Formula (XII). Likewise, the reaction depicted in Reaction Scheme 12 can be carried out in the same manner as described above with respect to Reaction Scheme 11.

Reaction Scheme 12

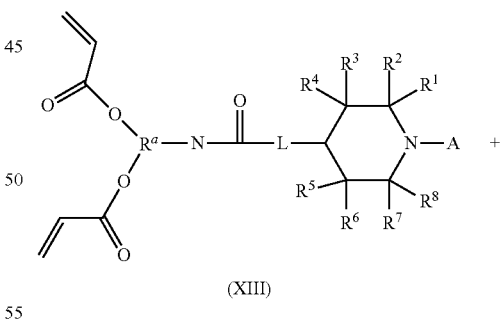

(XIII)

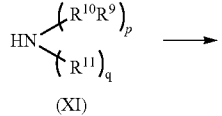

(XI)

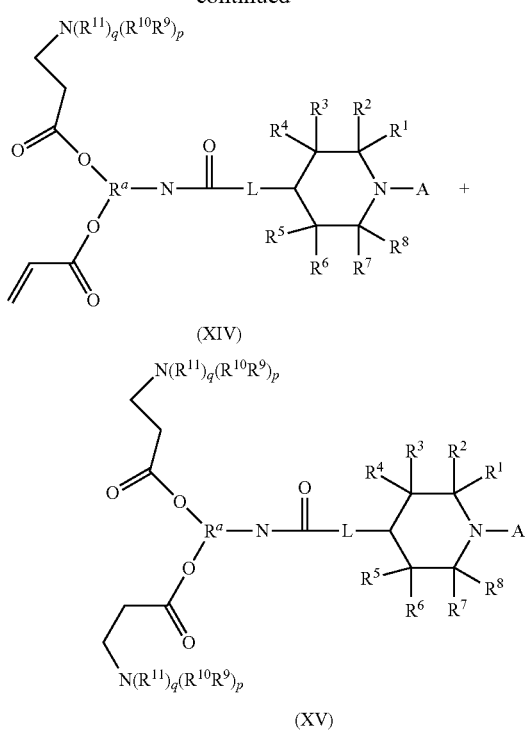

(XIV)

(XV)

A second approach can be used to make compounds of Formulas (I), (II), or (IIa) wherein $R^c$ is $R^9$. The second approach entails reacting a compound of Formula (III), such as a compound of Formula (IIIa), (IIIb), (IV), or (IVa), with an isocyanosilane, such as an isocyanoalkylsilane. The reaction between a compound of Formula (III) and an isocyanosilane of Formula (XVI) is illustrated in Reaction Scheme 13.

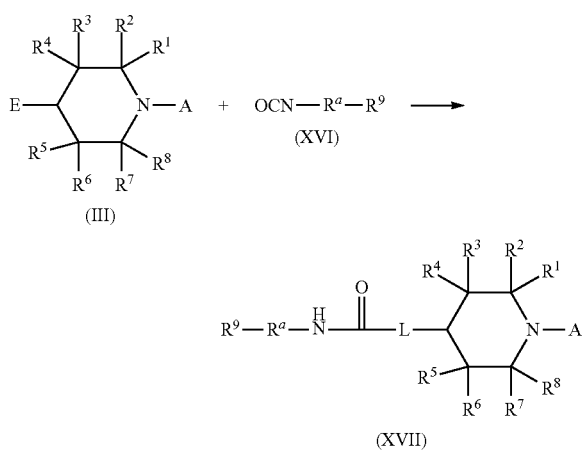

In Reaction Scheme 13, the compound of Formula (III) can be any compound of Formula (III), including any compound of Formula (IIIa), (IIIa1), (IIIa2), (IIIb), (IIIb1), (IIIb2), (IV), (IVa), (IV1), (IV2), (IV3), (IVa1), (IVa2), or (IVa3). Thus, the identity of A, E, and $R^1$ to $R^5$ is the same as that discussed above for those compounds.

In the compound of Formula (XVI), $R^a$ and $R^9$ are defined as discussed above with reference to the compound of Formula (I). In many cases, $R^a$ is alkylene, such as $C_1$-$C_{12}$ alkylene or $C_1$-$C_6$ alkylene.

The reaction illustrated in Reaction Scheme 13 can be carried out by any method suitable for condensing an isocyanato group with the exocyclic alcohol or amine of the compound of Formula (III) that is used. Typically, the starting materials are admixed at a temperature sufficient to promote the reaction, which is often from 50° C. to 100° C. The reactants can be stirred at the elevated temperature until the reaction is complete, which typically takes between 1 hour and 12 hours. The progress of the reaction can be monitored by FTIR; when FTIR analysis of the reaction mixture shows no prominent isocyanate absorbance at about 2250 cm$^{-1}$ to 2275 cm$^{-1}$, such as 2265 cm$^{-1}$, the reaction is typically complete.

The reaction illustrated in Reaction Scheme 13 can take place under dry conditions in order to minimize the formation of unwanted byproducts. In many cases, an inert diluent is used. The inert diluent is typically a liquid that can dissolve or disperse the compounds of Formula (III) and (XVI) but does not undergo chemical transformation under the reaction conditions. Typical inert diluents include ketones such as acetone and methyl ethyl ketone, chlorinated compounds such as chloroform and dichloromethane, and aromatic compounds such as benzene, toluene, and xylenes. Tin catalyst, amine catalyst, or both are often used, as discussed above with respect to Reaction Schemes 6, 7, 8, 9, and 10.

One or more of the compounds discussed herein, such as any compound of Formulas (I), (II), and (IIa), can be used to mitigate the adverse effects of actinic radiation, such as visible or ultraviolet light, in a substrate such as glass or ceramic. The silane groups of the compounds discussed herein can be affixed to the glass or ceramic substrate, thereby providing the substrate with resistance to the adverse effects of actinic radiation, such as adverse effects of visible or ultraviolet light. Affixing silane groups to glass or ceramic substrates is well known to the person of ordinary skill in the art, and can be accomplished by any suitable method.

In some embodiments, the compound of Formulas (I), (II), and (IIa) can be affixed to silica nanoparticles. The silica nanoparticles can then be incorporated into ceramics, polymer coatings, polymer or ceramic articles, and the like.

When one or more compounds discussed herein contain an ethylenically unsaturated double bond, the compound can be co-polymerized with one or more other ethylenically unsaturated monomers, such as (meth)acrylates, (meth)acrylics, styrenyl monomers, vinyl monomers, and the like. This polymerization can occur either neat, in solution or dispersion, or on the surface of a substance, such as a glass or ceramic substance, to which the compound is bound.

Articles, such as glass, ceramic, or polymer articles, can comprise one or more of the compounds discussed herein. Such articles can be resistant to the damaging effects of actinic radiation, such as ultraviolet or visible light.

LIST OF EXEMPLARY EMBODIMENTS

The following list of embodiments is intended to better illustrate particular aspects of the disclosure. None of the embodiments enumerated below are intended to be limiting, unless otherwise specified.

Embodiment 1 is a compound having the structure of Formula (I):

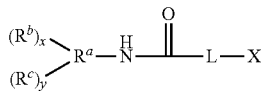

wherein:
X is

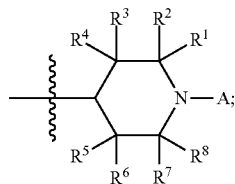

$R^1$ is alkyl;
$R^2$ is alkyl;
$R^3$ is H or alkyl;
$R^4$ is H or alkyl;
$R^5$ is H or alkyl;
$R^6$ is H or alkyl;
$R^7$ is alkyl; and
$R^8$ is alkyl;
A is alkyl or oxyalkyl;
L is O or NR';
R' is H or $C_1$ to $C_4$ alkyl;
x is 0-5 and y is 1-6, with the proviso that x+y is no greater than 6;
$R^a$ is a connecting group having a valence of x+y+1;
$R^b$ is an (alkyl)acrylolyoxy group functional group of the formula $OC(O)C(R^d)=CH_2$;
each $R^d$ is independently selected from alkyl and H;
$R^c$ is selected from $R^9$ and $—OC(O)CH(R^d)CH_2N(R^{10}R^9)_p(R^{11})_q$;
$R^9$ is $—Si(R^{12})_3$;
$R^{12}$ is selected from oxyalkyl, hydroxyl, $OC(O)R^d$, and alkyl with the proviso that at least one $R^{12}$ is oxyalkyl, $OC(O)R^d$, or hydroxyl;
$R^{10}$ is alkylene bound to $R^9$ and the N atom of the $—OC(O)CH(R^d)CH_2N$ moiety;
$R^{11}$ is alkyl or H bound to the N atom of the $—OC(O)CH(R^d)CH_2N$ moiety;
p represents the number of $R^{10}R^9$ groups, which can be 1 or 2; and
q represents the number of $R^{11}$ groups, which can be 0 or 1, with the proviso that the sum of p and q is 2.

Embodiment 2 is a compound of embodiment 1 having the structure of Formula (II).

Embodiment 3 is a compound of embodiment 1 having the structure of Formula (IIa).

Embodiment 4 is a compound of any of the preceding embodiments wherein A is alkyl.

Embodiment 5 is a compound of embodiment 4 wherein A is $C_1$ to $C_{12}$ alkyl.

Embodiment 6 is a compound of embodiment 5 wherein A is $C_1$ to $C_6$ alkyl.

Embodiment 7 is a compound of embodiment 6 wherein A is methyl.

Embodiment 8 is a compound of any of embodiments 1-3 wherein A is oxyalkyl.

Embodiment 9 is a compound of embodiment 8 wherein A is $C_1$ to $C_{12}$ oxyalkyl.

Embodiment 10 is a compound of embodiment 9 wherein A is $C_8$ oxyalkyl.

Embodiment 11 is a compound of any of the preceding embodiments wherein $R^1$ is $C_1$ to $C_6$ alkyl.

Embodiment 12 is a compound of embodiment 11 wherein $R^1$ is methyl.

Embodiment 13 is a compound of any of the preceding embodiments wherein $R^2$ is $C_1$ to $C_6$ alkyl.

Embodiment 14 is a compound of embodiment 13 wherein $R^2$ is methyl.

Embodiment 15 is a compound of any of the preceding embodiments wherein $R^3$ is H.

Embodiment 16 is a compound of any of the preceding embodiments wherein $R^4$ is H.

Embodiment 17 is a compound of any of the preceding embodiments wherein $R^5$ is H.

Embodiment 18 is a compound of any of the preceding embodiments wherein $R^6$ is H.

Embodiment 19 is a compound of any of the preceding embodiments wherein R' is $C_1$ to $C_6$ alkyl.

Embodiment 20 is a compound of embodiment 19 wherein $R^7$ is methyl.

Embodiment 21 is a compound of any of the preceding embodiments wherein $R^8$ is $C_1$ to $C_6$ alkyl.

Embodiment 22 is a compound of any of embodiment 21 wherein $R^8$ is methyl.

Embodiment 23 is a compound of any of the preceding embodiments wherein $R^a$ is polyvalent hydrocarbon.

Embodiment 24 is a compound of embodiment 23 wherein the polyvalent hydrocarbon is $C_1$ to $C_{12}$ polyvalent hydrocarbon.

Embodiment 25 is a compound of embodiment 24 wherein the polyvalent hydrocarbon is $C_1$ to $C_6$ polyvalent hydrocarbon.

Embodiment 26 is a compound of any of embodiments 1-22 wherein $R^a$ is alkylene.

Embodiment 27 is a compound of embodiment 26 wherein the alkylene is $C_1$ to $C_{12}$ alkylene.

Embodiment 28 is a compound of embodiment 27 wherein the alkylene is $C_1$ to $C_6$ alkylene.

Embodiment 29 is a compound of any preceding embodiment wherein $R^b$ is an (alkyl)acrylolyoxy functional group of the formula $OC(O)(R^d)=CH_2$ and $R^d$ is alkyl.

Embodiment 30 is a compound of embodiment 29 wherein the alkyl is $C_1$ to $C_6$ alkyl.

Embodiment 31 is a compound of embodiment 30 wherein the alkyl is methyl.

Embodiment 32 is a compound of any of embodiments 1-28 wherein $R^b$ is an (alkyl)acrylolyoxy functional group of the formula $OC(O)(R^d)=CH_2$ and $R^d$ is H.

Embodiment 33 is a compound of any of the preceding embodiments wherein x is 0.

Embodiment 34 is a compound of any of embodiments 1-32 wherein x is 1.

Embodiment 35 is a compound of any of embodiments 1-32 wherein x is 2.

Embodiment 36 is a compound of any of embodiments 1-32 wherein x is 3.

Embodiment 37 is a compound of any of embodiments 1-32 wherein x is 4.

Embodiment 38 is a compound of any of embodiments 1-32 wherein x is 5.

Embodiment 39 is a compound of any of embodiments 1-32 wherein x is 0 to 2.

Embodiment 40 is a compound of embodiment 39 wherein x is 0 or 1.

Embodiment 41 is a compound of any of the preceding embodiments wherein y is 1.

Embodiment 42 is a compound of any of the embodiments 1-40 wherein y is 2.

Embodiment 43 is a compound of any of the embodiments 1-40 wherein y is 3.

Embodiment 44 is a compound of any of the embodiments 1-40 wherein y is 4.

Embodiment 45 is a compound of any of the embodiments 1-40 wherein y is 5.

Embodiment 46 is a compound of any of the embodiments 1-40 wherein y is 6.

Embodiment 47 is a compound of any of the embodiments 1-40 wherein y is 1 to 4.

Embodiment 48 is a compound of any of the embodiments 1-40 wherein y is 1 or 2.

Embodiment 49 is a compound of any of the preceding embodiments wherein L is O.

Embodiment 50 is a compound of any of embodiments 1-48 wherein L is NR'.

Embodiment 51 is a compound of embodiment 50 wherein R' is H.

Embodiment 52 is a compound of embodiment 50 wherein R' is $C_1$ to $C_4$ alkyl.

Embodiment 53 is a compound of any of the preceding embodiments wherein at least one $R^{12}$ is oxyalkyl.

Embodiment 54 is a compound of embodiment 53 wherein each $R^{12}$ is oxyalkyl.

Embodiment 55 is a compound of any of embodiments 53 or 54 wherein the oxyalkyl is $C_1$ to $C_4$ oxyalkyl.

Embodiment 56 is a compound of embodiment 55 wherein the oxyalkyl is oxymethyl or oxyethyl.

Embodiment 57 is a compound of embodiment 56 wherein the oxyalkyl is oxymethyl.

Embodiment 58 is a compound of embodiment 57 wherein the oxyalkyl is oxyethyl.

Embodiment 59 is a compound of any of embodiments 1-53 wherein at least one $R^{12}$ is hydroxyl.

Embodiment 60 is a compound of any of the preceding embodiments wherein $R^c$ is $R^9$.

Embodiment 61 is a compound of any of embodiments 1-59 wherein $R^c$ is —OC(O)CH($R^d$)CH$_2$N($R^9R^{10}$)$_p$($R^{11}$)$_q$.

Embodiment 62 is a compound of embodiment 61 wherein $R^d$ is H.

Embodiment 63 is a compound of embodiment 61 wherein $R^d$ is alkyl.

Embodiment 64 is a compound of embodiment 63 wherein the alkyl is $C_1$ to $C_4$ alkyl.

Embodiment 65 is a compound of embodiment 64 wherein the alkyl is methyl.

Embodiment 66 is a compound of any of the preceding embodiments wherein $R^{11}$ is $C_1$ to $C_{12}$ alkyl.

Embodiment 67 is a compound of embodiment 66 wherein $R^{11}$ is $C_1$ to $C_6$ alkyl.

Embodiment 68 is a compound of embodiment 67 wherein $R^{11}$ is methyl.

Embodiment 69 is a compound of any of embodiments 1-65 wherein $R^{11}$ is H.

Embodiment 70 is a compound of any of the preceding embodiments wherein p is 1.

Embodiment 71 is a compound of any of embodiments 1-69 wherein p is 2.

Embodiment 72 is a compound of any of embodiments 1-70 wherein q is 0.

Embodiment 73 is a compound of any of embodiments 1-71 wherein q is 1.

Embodiment 74 is a substrate having a compound of any of the preceding embodiment affixed thereto.

Embodiment 75 is the substrate of embodiment 74 wherein the substrate comprises glass.

Embodiment 76 is the substrate of any of embodiments 74-75 wherein the substrate comprises ceramic.

Embodiment 77 is polymer derived from one or more compounds of any of embodiments 1-73.

Embodiment 78 is a nanoparticle comprising silica and having one or more of compounds of any of embodiments 1-73 affixed thereto.

Embodiment 79 is an article comprising one or more of a compound of any of embodiment 1-73, a substrate of any of embodiments 74-76, a polymer of embodiment 77, or a nanoparticle of embodiment 78.

EXAMPLES

Materials 1,2,2,6,6-pentamethyl-4-hydroxy-piperidine (PMHP) was obtained from TCI America, Portland, Oreg.

TINUVIN 123, IRGACURE 184, and IRGACURE 819 were obtained from BASF Florham Park, N.J. under trade designations "TINUVIN 123", "IRGACURE 184", and "IRGACURE 819", respectively.

1,1-bis(acryloyloxymethyl) ethyl isocyanate (BEI), isocyanatoethyl acrylate (AOI), and isocyanatoethyl methacrylate (MOI), were obtained from CBC America Corp., Commack, N.Y.

Bis-(3-trimethoxysilylpropyl)amine was obtained from Evonik, Piscataway, N.J. under trade designation "DYNASLAN 1124", or alternatively, from Momentive, Huntersville, N.C. as "SILQUEST 1170".

TEGORAD 2100 was obtained from Evonik, Piscataway, N.J. under trade designation "TEGORAD 2100".

Aminopropyltrimethoxysilane was obtained from Evonik, Piscataway, N.J. under trade designation "DYNASLAN AMMO".

N-methylaminopropyltrimethoxysilane and isocyanatopropyltriethoxysilane were obtained from Gelest, Morrisville, Pa. under trade designation "SIM6500.0-25GM" and "SII6455.0", respectively.

Isocyanatopropyltrimethoxysilane was obtained from Wacker, Adrian, Mich. under trade designation "GENIOSIL GF-40".

Tetrahydrofuran (THF), methyl ethyl ketone (MEK), methyl t-butyl ether (MTBE), sodium carbonate, sodium hydroxide, anhydrous magnesium sulfate, 85% potassium hydroxide, dimethylsulfoxide (DMSO), methylene chloride (dichloromethane), methanol, chloroform, and triethyl amine were obtained from EMD Chemicals, Gibbstown, N.J.

Hydroxyethyl acrylate (HEA), 4-methoxy phenol (MEHQ), triethylamine, dibutyltindilaurate (DBTDL), acryloyl chloride, oxalyl chloride, and sodium cyanoborohydride were obtained from Sigma-Aldrich, Milwaukee, Wis.

Ammonium acetate was obtained from VWR, West Chester, Pa.

EBECRYL 600, epoxy acrylate of the diglycidyl ether of bisphenol A, was obtained from Allnex, Alpharetta, Ga. under trade designation "EBECRYL 600".

Hexanediol diacrylate was obtained from Sartomer Company of Exton, Pa. under the designation "SR238".

Acrylated Benzotriazole CAS number 96478-09-0, was obtained from TCI America, Portland, Oreg.

4-hydroxytempo was obtained from BASF in Florham Park, N.J. under trade designation "PROSTAB 5198".

1-methoxy-2-propanol was obtained from Alfa Aesar in Ward Hill, Mass.

Methacryloylpropyl trimethoxysilane was obtained from Dow Corning in Midland, Mich. under trade designation "Z-6030".

1-methoxy-2,2,5,5-tetramethylpiperidin-4-ol was prepared using a procedure reported by Schoening et al. (J. Org. Chem., 2009, 74, 1567-1573).

NALCO 2327 (colloidal silica dispersion in water) was obtained from Nalco Company in Naperville, Ill. under trade designation "NALCO 2327".

20 nm silica particles functionalized with 3-methacryloxypropyltrimethoxysilane were prepared by the method described in U.S. Pat. No. 7,101,616 (column 16 lines 5-17).

Preparative Example 1

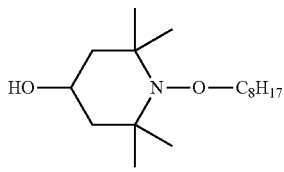

A 1 L 3-necked round bottom flask equipped with overhead stirrer and a vacuum bearing was charged with 200 g (0.275 mol, 0.55 eq, 737 MW) TINUVIN 123, and 323 g ethanol and placed in an oil bath at 70° C. To the reaction was added 73.23 g (1.109 mol, 66.01 MW) 85% potassium hydroxide. As the base was added the color of the reaction mixture changed from yellow to orange to brown; the reaction mixture also began refluxing. The bottom of the flask was scraped to provide a homogeneous mixture.

After the reaction mixture refluxed for 3.5 hours, the flask was fitted with a distillation head and condenser and placed under aspirator vacuum. 215 g of ethanol was collected by distillation, after which the reaction mixture was a thick, taffy-like mass. 250 g of water was added to the reaction mixture and the inside of the flask was scraped to disperse or dissolve the solids. The mixture was stirred for about 10 min at about 50° C., after which 300 g MTBE was added to the flask with additional stirring for 10 min. The reaction mixture was then poured into a 2 L separatory funnel, the bottom layer drained off and the top layer washed with 250 g water in the funnel. After removing the aqueous layer, the organic layer was dried over anhydrous magnesium sulfate, filtered, and concentrated on a rotary evaporator under aspirator pressure at 90° C. for 2 h to provide 137.2 g (87%) of undistilled product. This was distilled at 140° C. (pot temperature) at 29.3 Pa to provide 127.5 g (80.8%) of product.

Preparative Example 2

Preparation of a Ketone Intermediate

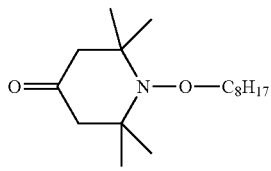

To a 500 mL 3-neck flask equipped with overhead stirrer and nitrogen inlet adapter, and rubber septum was charged 12.04 g (0.1541 mol) dimethyl sulfoxide and 226 g of methylene chloride. The reaction was put under a nitrogen atmosphere and placed in an isopropanol dry-ice bath. After a few minutes, 9.78 g (0.0770 mol) oxalyl chloride was added via syringe through the septum over one minute. Five minutes later 20.00 g (0.0701 mol, approximate molecular weight 285.47) 2,2,6,6-tetramethyl-4-hydroxy-1-octyloxy-piperidine (the product of Preparative Example 1) was slowly added by syringe through the septum over 15 minutes. After 15 minutes of further stirring, 17.72 g (0.17515 mol) triethylamine was added by syringe over about 30 seconds. Stirring was continued for 10 minutes in the isopropanol/dry ice bath, followed by an additional 10 minutes at room temperature. The resulting solution was washed with 333 mL of 2-N hydrochloric acid, providing a mixture with distinct organic and aqueous layers. The organic and aqueous layers were separated, and the aqueous layer was extracted with 200 g of chloroform. The chloroform was combined with the other organic layer, and combined organic layers were dried over anhydrous magnesium sulfate, filtered, and concentrated on a rotary evaporator under water aspirator pressure at about 65° C. for 2 hours to provide an oil. The product was evaluated by $^1$H NMR and FTIR, which gave results consistent with the expected structure.

Preparative Example 3

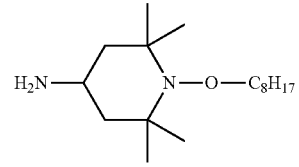

A 250 mL 3-necked flask equipped with overhead stirrer was charged with 5.00 g (0.017639 mol) 2,2,6,6-tetramethyl-4-keto-1-octyloxy-piperidine (the product of Preparative Example 2) 8 g of 3 angstrom molecular sieves, 13.60 g (0.17639 mol) ammonium acetate, and 77.5 g methanol and stirred for 1.75 hours under nitrogen at room temperature, after which 1.51 g (0.0242 mol) sodium cyanoborohydride in 13 g methanol was added to the reaction over 45 minutes and allowed to stir overnight. 360 g chloroform was then added to the reaction mixture and the mixture was washed twice with 400 g of 1N sodium hydroxide, dried over anhydrous magnesium sulfate, filtered, and concentrated at 40° C. at aspirator pressure on a rotary evaporator. Analysis by $^1$H NMR showed the reaction to be a mixture of about 70 mole percent of the desired amine, 18 mole percent of a secondary amine, and 12 mole percent of the starting material. The products were separated to flash chromatography using an Analogix Intelliflash 280 from Agilent Technologies, Inc., Santa Clara, Calif. with a 150 g, 40 mm diameter column using a gradient of 25-30% methanol in methylene chloride over 20 minutes and then 30% methanol in methylene chloride to provide the desired product (2,2,6,6-tetramethyl-4-amino-1-octyloxy-piperidine) as an oil.

Preparative Example 4

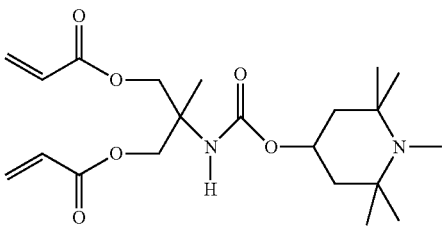 [SMILES: C=CC(=O)OCC(C)(COC(=O)C=C)NC(=O)OC1CC(C)(C)N(C)C(C)(C)C1]

A three-necked 500 mL round bottom flask equipped with stir bar was charged with 44.18 g (0.2579 mol) PHMP, which was dried according the procedure discussed above in Example 1. The flask was then placed in a 75° C. oil bath under dry air. When the PHMP fully molted, the flask was charged with 633 microliters DBTDL (2,000 ppm). Using an addition funnel, 61.71 g (0.2579 mol) BEI was charged into the reaction over 20 minutes. After 30 minutes, FTIR analysis of the reaction showed no isocyanate absorption at 2265 cm$^{-1}$, and the product was obtained an oil.

Preparative Example 5

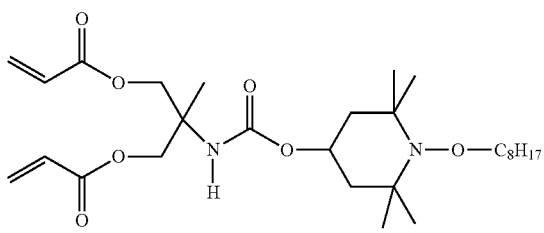

A procedure analogous to that of Preparative Example 4 was followed, except that 24.98 g (0.0875 mol) 2,2,6,6-tetramethyl-4-hydroxy-1-octyloxy-piperidine (the product of Preparative Example 1) 22.44 g (0.0937 mol) BEI, 8.86 g (0.0875 mol) triethylamine, and 270 microliters of DBTDL in MEK were used in the reaction mixture.

Preparatory Example 6

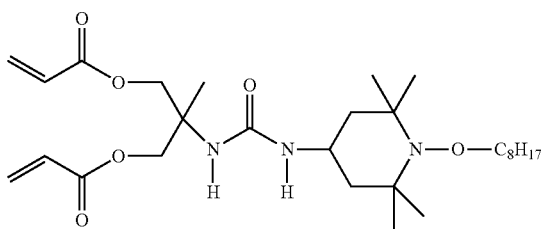

A vial was charged with 0.50 g (0.00209 mol) BEI, 2.0 g methylene chloride and 6 microliter 10% DBTDL in methylene chloride (~500 ppm based on total solids) and placed in an ice water bath. Next, a solution of 0.59 g (0.00209 mol) of the product of Preparative Example 3 in 3.26 g methylene chloride was added to the vial over about 7 min. An aliquot taken immediately after addition was analyzed by FTIR and found to have a small isocyanate peak at about 2265 cm$^{-1}$. A sample taken at 16 min was analyzed by FTIR was unchanged. At 23 min, 0.010 g more amine was added to the reaction.

At 43 min, FTIR analysis showed no isocyanate peak. The material was concentrated on a rotary evaporator to provide a thick oil, and its identity was confirmed by $^1$H NMR analysis.

Example 1

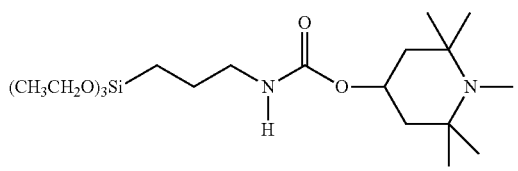

A 250 mL round bottom flask equipped with stir bar was charged 3.81 g (0.022244 mol) of dried PHMP, 5.50 g (0.022244 mol) isocyanatopropyltriethoxysilane, and 70 microliters of a 10% solution of DBTDL in MEK and placed in a 75° C. oil bath under dry air. After 2.5 h, the FTIR analysis of the reaction showed no isocyanate peak at 2265 cm$^{-1}$, providing an oil whose identity was confirmed by $^1$H NMR analysis.

Example 2

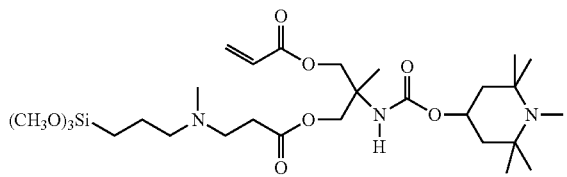

A vial equipped with a stir bar and containing 1.19 g (0.002898 mol) of the product Preparative Example 4 was charged with 0.56 g (0.002898 mol) N-methylaminopropyltrimethoxysilane followed by 1.75 g methylene chloride and placed in a 45° C. bath for about 22 h. The material was concentrated on a rotary evaporator to provide a thick oil whose identity was confirmed by $^1$H NMR analysis.

Example 3

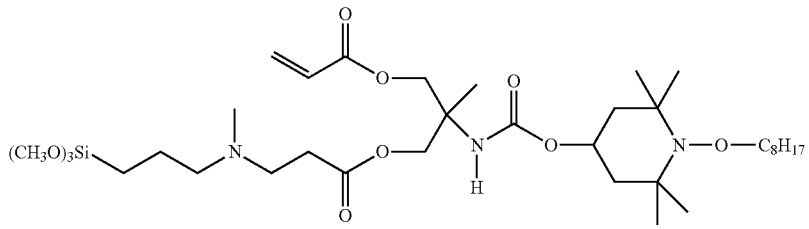

A vial equipped with a stir bar and containing 1.00 g (0.00191 mol) of the product of Preparative Example 5 was charged with 0.37 g (0.00191 mol) N-methylaminopropyltrimethoxysilane followed by 1.37 g methylene chloride and placed in a 45° C. bath for 22 h. The material was concentrated on a rotary evaporator to provide a thick oil whose identity was confirmed by $^1$H NMR analysis.

Example 4

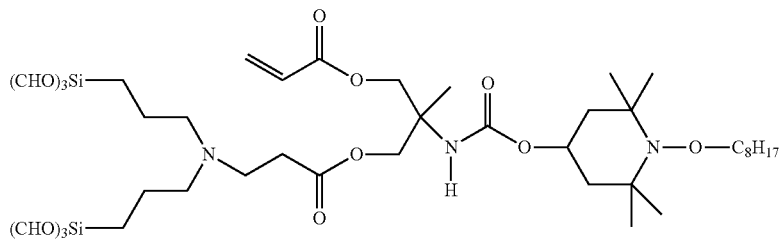

A vial equipped with a stir bar was charged with 1.00 g (0.00191 mol) of the product of Preparative Example 5, 0.65 g (0.00191 mol) DYNASYLAN 1124, and 1.65 g methylene chloride, and was placed in a 45° C. bath for about 22 h. The material was concentrated on a rotary evaporator to provide an oil whose identity was confirmed by $^1$H NMR analysis.

Example 5

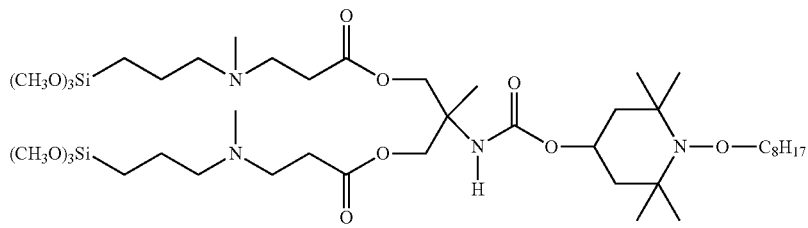

A vial equipped with a stir bar and containing 1.00 g (0.00191 mol) of the product of Preparative Example 5 was charged with 0.74 g (0.003811 mol) N-methylaminopropyltrimethoxysilane followed by 1.74 g methylene chloride and placed in a 45° C. bath for about 22 h. The material was concentrated on a rotary evaporator to provide a thick oil whose identity was confirmed by $^1$H NMR analysis.

Example 6

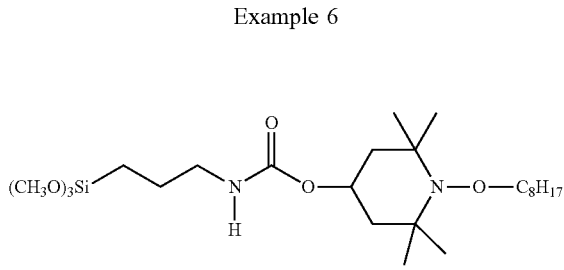

A 100 mL round bottom flask was charged with 5.02 g (0.0175 mol) of the product of Preparative Example 1, 1.78 g (0.0175 mol, 101.19 MW) triethylamine, and 3.79 g (0.0183 mol, 205.29 MW) 3-isocyanatopropyltrimethoxysilane, 122 microliters of a 10% by weight solution of DBTDL in MEK, and stir bar, and heated at 75° C. for 1 h under dry air. At the end of that time FTIR analysis showed no —NCO absorption at 2265 cm$^{-1}$ and the triethylamine was removed on a rotary evaporator under aspirator.

Example 7

A 100 mL round bottom flask was charged with 5.02 g (0.0175 mol) of the product of Preparative Example 1, 1.77 g (0.0175 mol, 101.19 MW) triethylamine, and 4.54 g (0.0183 mol, 247.37 MW) 3-isocyanatopropyltriethoxysilane, 131 microliters of a 10% by weight solution of DBTDL in MEK, and a stir bar, and heated at 75° C. for 1 h under dry air. At the end of that time FTIR analysis showed no —NCO absorption at 2265 cm$^{-1}$, triethylamine was removed on a rotary evaporator under aspirator pressure.

Example 8

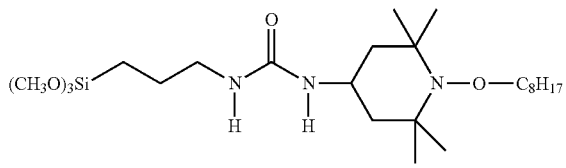

A vial was charged with 0.50 g (0.002436 mol) isocyanatopropyltrimethoxysilane, 1.16 g methylene chloride and 5 microliter 10% DBTDL in methylene chloride (~500 ppm based on total solids). Next, a solution of 0.69 g (0.002436 mol) of the product of Preparatory Example 3 in 1.61 g methylene chloride was added to the vial over 2 min. An aliquot taken immediately after addition was analyzed by FTIR and analysis showed no isocyanate peak at 2265 cm$^{-1}$. The material was concentrated on a rotary evaporator to provide a thick oil whose identity was confirmed by $^1$H NMR analysis.

Example 9

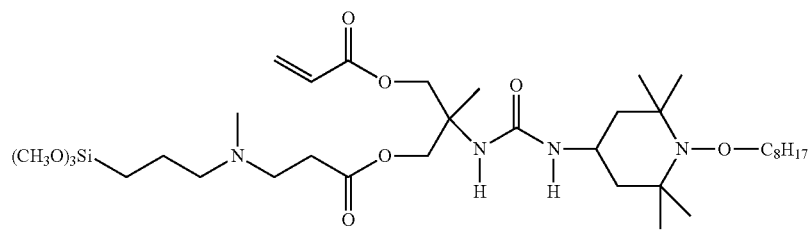

A vial equipped with a stir bar and containing 0.455 g (0.000868 mol) of the product of Preparative Example 6 was charged with 0.168 g (0.000868 mol) N-methylaminopropyltrimethoxysilane followed by 1.5 g methylene chloride and placed in a 40° C. bath for 16.5 h. The material was concentrated on a rotary evaporator to provide a thick oil whose identity was confirmed by $^1$H NMR analysis.

Example 10

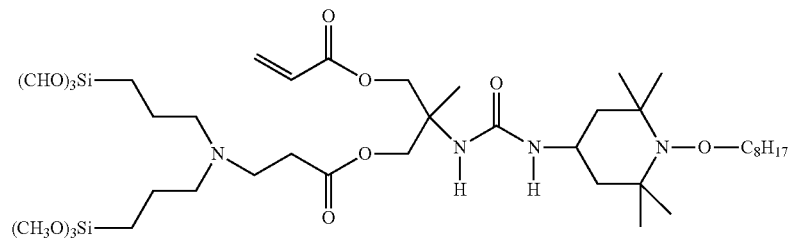

A vial equipped with a stir bar was charged with 0.403 g (0.000077 mol) of the product of Preparative Example 6, 0.263 g (0.000077 mol) DYNASYLAN 1124, and 1.5 g methylene chloride, and placed in a 40° C. bath for about 16 h. The material was concentrated on a rotary evaporator to provide an oil whose identity was confirmed by $^1$H NMR analysis.

Example 11

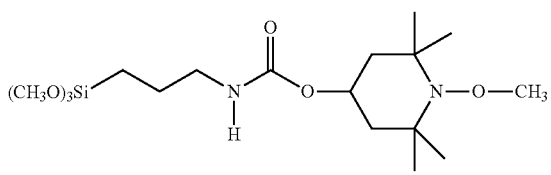

A 100 mL nitrogen-purged round-bottomed flask with condenser attached was charged with 1-methoxy-2,2,5,5-tetramethylpiperidin-4-ol (5.37 g, 28.7 mmol), isocyanatopropyl trimethoxysilane (5.89 g, 28.7 mmol), and triethylamine (3.19 g, 31.6 mmol). The resulting solution was heated in a 50° C. oil bath and stirred for 2 hours. The temperature of the oil bath was then increased to 80° C. and stirring was continued for an additional 3 hours. Analysis of the reaction mixture by FTIR suggested complete consumption of the isocyanate. The solution was then concentrated at reduced pressure to yield 10.4 g of brown oil.

Example 12

Functionalized Silica Particles

A colloidal silica dispersion was prepared by charging a 2 L round-bottom flask with 400 g of NALCO 2327 and a first portion of 500 mL of 1-methoxy-2-propanol. The mixture was concentrated under reduced pressure to about 500 mL. A second 500 mL portion of 1-methoxy-2-propanol was added, and the mixture was again concentrated under reduced pressure to about 500 mL. A third portion of 1-methoxy-2-propanol was added, and the mixture was again concentrated to approximately 800 mL total volume. The resulting dispersion contained, by weight, 19.5% silica and 3.3% water in 1-methoxy-2-propanol.

A 1 L round-bottom flask was charged with 200.5 g of the colloidal silica dispersion described above, 4.98 g of methacyrloylpropyltrimethoxysilane, and 0.115 g of 4-hydroxytempo. A mixture of 2.07 g of the product of Example 6 and 10 g of 1-methoxy-2-propanol was added. The resulting mixture was heated at reflux for 24 hours. The resulting liquid was hazy and opalescent, and contained 20.3% solids by mass as determined by measuring mass loss upon evaporation of a known-volume aliquot to dryness. This liquid was used without further modification.

Example 13

Coatings Comprising Functionalized Silica Particles

Solution 1 was prepared from 28 g EBECRYL 600, 7 g SR238, 73.89 g of a 20.3% solids solution of 20 nm silica particles prepared according to Example 12 as described above, with 1.0 g IRGACURE 184, 0.5 g IRGACURE 819, 1.0 g of a 10% solution of TEGORAD 2100 in MEK, and 18.36 g 1-methoxy-2-propanol.

Solution 2 was prepared by taking 30 g of Solution 1 and adding 1.16 g of a 10% by solids solution of Acrylated Benzotriazole CAS number 96478-09-0 UVA in MEK.

Each solution was coated onto 4 mil (100 micrometer) primed PET (obtained from E.I. DuPont de Nemours and Company, Wilmington, Del., commercially available under the trade designation "MELINEX 618") using a #10 wire wound bar and dried at 80° C. for 2 minutes.

The dried coating having a thickness of about 6 microns was then cured with HP-6 High Powered Six-Inch UV Lamp System with VPS-3 Power Supply using a 300 w/in Fusion H bulb (both system and bulb from Heraeus Noblelight Fusion UV Inc., Gaithersburg, Md.) at 100% power, under nitrogen at 30 feet/min (9.14 m/min). The coatings were clear and colorless hardcoats.

What is claimed is:

1. A compound having the structure of Formula (I):

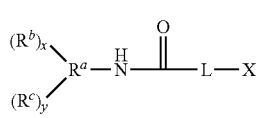

wherein:

X is

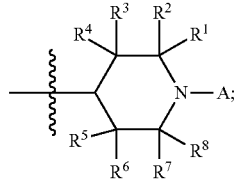

$R^1$ is alkyl;
$R^2$ is alkyl;
$R^3$ is H or alkyl;
$R^4$ is H or alkyl;
$R^5$ is H or alkyl;
$R^6$ is H or alkyl;
$R^7$ is alkyl;
$R^8$ is alkyl;
A is alkyl or oxyalkyl;
L is O or NR';
R' is H or $C_1$ to $C_4$ alkyl;
x is 0-5 and y is 1-6, with the proviso that x+y is no greater than 6;
$R^a$ is a connecting group having a valence of x+y+1, wherein the connecting group is an alkane-diyl, alkane-triyl, or a polyvalent hydrocarbon;
$R^b$ is an (alkyl)acrylolyoxy functional group of the formula $OC(O)C(R^d)$=$CH_2$;
each $R^d$ is independently selected from alkyl and H;
$R^c$ is —$OC(O)CH(R^d)CH_2N(R^{10}R^9)_p(R^{11})_q$;
$R^9$ is —$Si(R^{12})_3$, and $R^{12}$ is selected from oxyalkyl, hydroxyl, $OC(O)R^d$, and alkyl with the proviso that at least one $R^{12}$ is oxyalkyl, $OC(O)R^d$, or hydroxyl;
$R^{10}$ is alkylene bound to $R^9$ and the N atom of the —$OC(O)CH(R^d)CH_2N$ moiety;
$R^{11}$ is alkyl or H bound to the N atom of the —$OC(O)CH(R^d)CH_2N$ moiety;
p represents the number of $R^{10}R^9$ groups, which can be 1 or 2; and
q represents the number of $R^{11}$ groups, which can be 0 or 1, with the proviso that the sum of p and q is 2.

2. The compound of claim 1 wherein $R^a$ is $C_1$ to $C_{12}$ alkylene.

3. The compound of claim 1 wherein L is O.

4. The compound of claim 1 wherein L is NR'.

5. The compound of claim 1 wherein A is alkyl.

6. The compound of claim 1 wherein A is oxyalkyl.

7. The compound of claim 1 wherein x is 0 or 1.

8. The compound of claim 1 wherein y is 1 or 2.

9. The compound of claim 1 wherein $R^1$, $R^2$, $R^7$, and $R^8$ are methyl and $R^3$, $R^4$, $R^5$, and $R^6$ are H.

10. A substrate or a nanoparticle having at least one compound of claim 1 affixed thereto.

11. A polymer derived from at least one compound of claim 1.

* * * * *

UNITED STATES PATENT AND TRADEMARK OFFICE
CERTIFICATE OF CORRECTION

PATENT NO. : 10,450,332 B2  
APPLICATION NO. : 16/114401  
DATED : October 22, 2019  
INVENTOR(S) : Klun et al.

Page 1 of 2

It is certified that error appears in the above-identified patent and that said Letters Patent is hereby corrected as shown below:

In the Specification

Column 2  
Line 28, Delete "(alkyl)acrylolyoxy" and insert -- (alkyl)acryloyloxy --, therefor.  
Line 32, Delete "$(R^{11})_q$," and insert -- $(R^{11})_q$; --, therefor.

Column 6  
Line 52, Delete "R'" and insert -- $R^1$ --, therefor.

Column 7  
Line 34, Delete "R'" and insert -- $R^1$ --, therefor.

Column 8  
Line 47, Delete "bis(alkyated" and insert -- bis(alkylated --, therefor.

Column 10  
Line 6, Formula (IIIb), Delete "N-Oxyakyl" and insert -- N-Oxyalkyl --, therefor.  
Line 19, Formula (IIId), Delete "N-Oxylkyl" and insert -- N-Oxyalkyl --, therefor.  
Line 19, Formula (IVa), Delete "N-Oxyalk" and insert -- N-Oxyalkyl --, therefor.  
Line 34, Delete "cyannoborohydride" and insert -- cyanoborohydride --, therefor.  
Line 38, Delete ""Cyanohydriodoborate" and insert -- "Cyanohydridoborate --, therefor.

Column 12  
Line 9, Delete "acrylolyloxy" and insert -- acryloyloxy --, therefor.  
Line 11, Delete "methacrylolyoxy." and insert -- methacryloyloxy. --, therefor.

Column 14  
Lines 31-32, Delete "bis(dimethyllaminoethyl)ether, morphonilin" and insert  
-- bis(dimethylaminoethyl)ether, morpholine --, therefor.  
Line 33, Delete "]oxtane" and insert -- ]octane --, therefor.

Signed and Sealed this  
Twenty-fourth Day of December, 2019

Andrei Iancu  
*Director of the United States Patent and Trademark Office*

CERTIFICATE OF CORRECTION (continued)
U.S. Pat. No. 10,450,332 B2

Lines 55-56, Delete "(alkyl)acrylolyoxy" and insert -- (alkyl)acryloyloxy --, therefor
Line 57, Delete "(alkyl)acrylolyoxy" and insert -- (alkyl)acryloyloxy --, therefor.

Column 15
Lines 2, 4 and 26, Delete "R'" and insert -- $R^1$ --, therefor.

Column 16
Line 14, Delete "—Si($R^2$)₃," and insert -- —Si($R^{12}$)₃, --, therefor.
Line 27, Delete "$R^1$'" and insert -- $R^{10}$ --, therefor.
Line 56, Delete "(alkyl)acrylolyoxy" and insert -- (alkyl)acryloyloxy --, therefor.

Column 17
Line 33, Delete "R'" and insert -- $R^1$ --, therefor.
Lines 37 and 47, Delete "(alkyl)acrylolyoxy" and insert -- (alkyl)acryloyloxy --, therefor.

Column 19
Line 66, Delete "$R^5$" and insert -- $R^8$ --, therefor.

Column 21
Line 37, Delete "(alkyl)acrylolyoxy" and insert -- (alkyl)acryloyloxy --, therefor.

Column 22
Line 23, Delete "R'" and insert -- $R^7$ --, therefor.
Lines 45 and 52, Delete "(alkyl)acrylolyoxy" and insert -- (alkyl)acryloyloxy --, therefor.

Column 24
Lines 34 and 39, Delete ""DYNASLAN" and insert -- "DYNASYLAN --, therefor.

Column 26
Line 46, After "2)" insert -- , --.

Column 27
Line 39, After "1)" insert -- , --.

Column 32
Line 65, Delete "methacyrloylpropytrimethoxysilane," and insert
-- methacryloylpropyltrimethoxysilane --, therefor.

In the Claims

Column 34
Line 19, In Claim 1, delete "(alkyl)acrylolyoxy" and insert -- (alkyl)acryloyloxy --, therefor.